US009351722B2

(12) United States Patent
Koogle, Jr. et al.

(10) Patent No.: US 9,351,722 B2
(45) Date of Patent: May 31, 2016

(54) DRIVE SYSTEM FOR TISSUE REPAIR

(71) Applicant: Arthrex, Inc., Naples, FL (US)

(72) Inventors: David C. Koogle, Jr., Bonita Springs, FL (US); Jake Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 610 days.

(21) Appl. No.: 13/725,059

(22) Filed: Dec. 21, 2012

(65) Prior Publication Data

US 2013/0178871 A1     Jul. 11, 2013

Related U.S. Application Data

(60) Provisional application No. 61/580,024, filed on Dec. 23, 2011.

(51) Int. Cl.
*A61B 17/04*     (2006.01)

(52) U.S. Cl.
CPC ......... *A61B 17/0491* (2013.01); *A61B 17/0401* (2013.01); *A61B 2017/0409* (2013.01); *A61B 2017/0417* (2013.01); *A61B 2017/0419* (2013.01)

(58) Field of Classification Search
CPC ............... A61B 17/04; A61B 17/0401; A61B 17/0469; A61B 17/0482; A61B 17/0487; A61B 2017/0409; A61B 2017/0417; A61B 2017/0419; A61B 2017/464; A61B 2017/048; A61B 2017/0488; A61F 2/08; A61F 2/0805; A61F 2/0811; A61F 2002/0817–2002/0894
USPC ....................................................... 606/232
See application file for complete search history.

(56) References Cited

U.S. PATENT DOCUMENTS 5,431,666 A * 7/1995 Sauer et al. .................... 606/139
5,810,848 A * 9/1998 Hayhurst ...................... 606/144
(Continued)

FOREIGN PATENT DOCUMENTS

EP     0589306     3/1994
EP     1484021     12/2004
(Continued)

OTHER PUBLICATIONS

European Patent Office, "Supplementary Partial European Search Report," issued in European patent application No. 1286084.6, dated Feb. 25, 2015, document of 5 pages.
(Continued)

*Primary Examiner* — David C Eastwood
(74) *Attorney, Agent, or Firm* — Akerman LLP; Michael K. Dixon

(57) ABSTRACT

A suture drive system configured to assist in attaching a suture to tissue within a patient, and in at least one application, repairing meniscal tears and shoulder tissue tears is disclosed. The suture drive system may be interchangeable in that the system can be adapted to insert different suture systems into tissue of a patient using the same device. In particular, in one embodiment configured to employ an inside-out suture delivery method, the suture drive system may advance two combinations of push rods and two swaged needles having one or more sutures attached thereto. In another embodiment configured to employ an outside-in suture delivery method, the suture drive system may advance two combinations of push rods and drive shafts to deliver two anchors releasably affixed to the distal ends of the drive shafts into tissue to close an opening in the tissue.

8 Claims, 31 Drawing Sheets

(56) References Cited

U.S. PATENT DOCUMENTS

| | | | |
|---|---|---|---|
| 7,862,572 B2 | 1/2011 | Meade et al. | |
| 7,947,053 B2 | 5/2011 | McKay et al. | |
| 8,070,818 B2 * | 12/2011 | Bhatnagar et al. | 623/17.16 |
| 8,083,803 B2 | 12/2011 | Albertorio et al. | |
| 8,128,640 B2 | 3/2012 | Harris et al. | |
| 8,298,247 B2 | 10/2012 | Sterrett et al. | |
| 8,353,915 B2 | 1/2013 | Helenbolt et al. | |
| 2003/0236535 A1 | 12/2003 | Onuki et al. | |
| 2005/0288689 A1 | 12/2005 | Kammerer et al. | |
| 2006/0030885 A1 | 2/2006 | Hyde | |
| 2006/0142799 A1 | 6/2006 | Bonutti | |
| 2006/0247643 A1 * | 11/2006 | Bhatnagar et al. | 606/75 |
| 2006/0293709 A1 * | 12/2006 | Bojarski | A61B 17/0401 606/232 |
| 2007/0027476 A1 | 2/2007 | Harris et al. | |
| 2007/0142846 A1 * | 6/2007 | Catanese et al. | 606/142 |
| 2008/0091220 A1 | 4/2008 | Chu | |
| 2008/0140092 A1 | 6/2008 | Stone et al. | |
| 2008/0275512 A1 | 11/2008 | Albertorio et al. | |
| 2009/0228026 A1 | 9/2009 | Koogle et al. | |
| 2009/0228042 A1 | 9/2009 | Koogle et al. | |
| 2009/0275950 A1 | 11/2009 | Sterrett et al. | |
| 2009/0326564 A1 * | 12/2009 | White et al. | 606/148 |
| 2010/0087857 A1 * | 4/2010 | Stone et al. | 606/232 |
| 2010/0137917 A1 | 6/2010 | Koogle | |
| 2010/0324608 A1 | 12/2010 | Albertorio et al. | |
| 2011/0213388 A1 | 9/2011 | Rioux | |
| 2011/0306989 A1 * | 12/2011 | Darois et al. | 606/144 |

FOREIGN PATENT DOCUMENTS

| | | |
|---|---|---|
| EP | 2098172 | 9/2009 |
| WO | 03/077772 | 9/2003 |

OTHER PUBLICATIONS

Patent Cooperation Treaty, "International Search Report and Written Opinion" U.S. International Searching Authority, by Officer Thomas, Shane, in PCT Application No. PCT/US2012/071406, Document of 9 pages, dated Mar. 13, 2013.

* cited by examiner

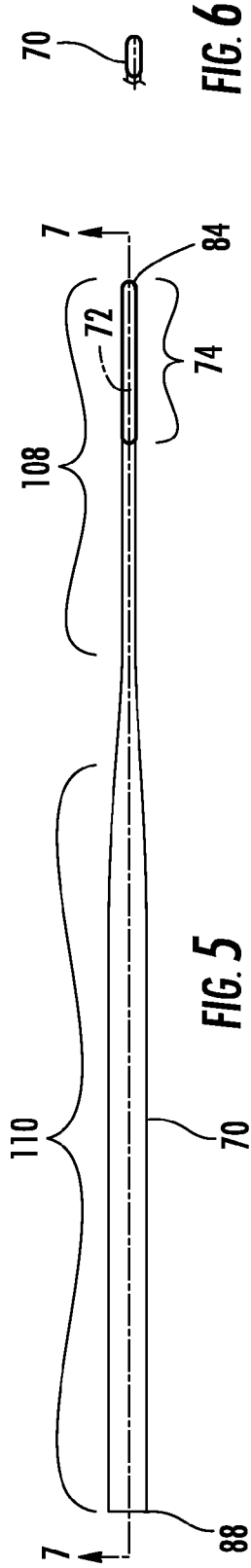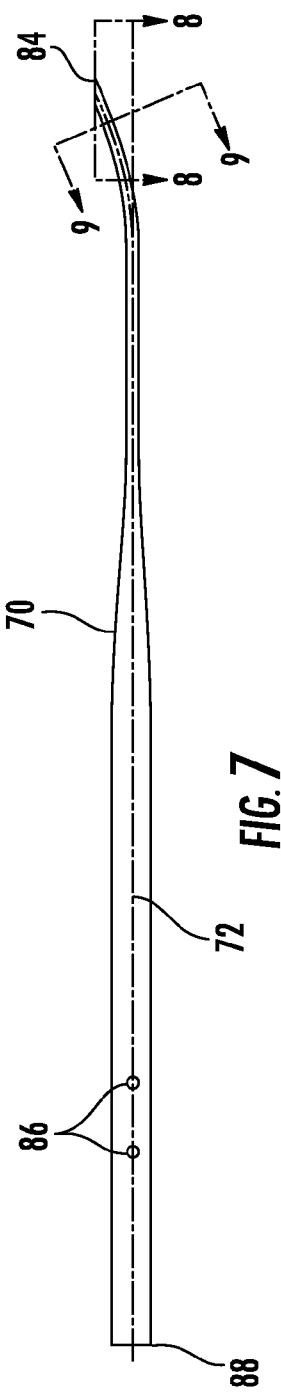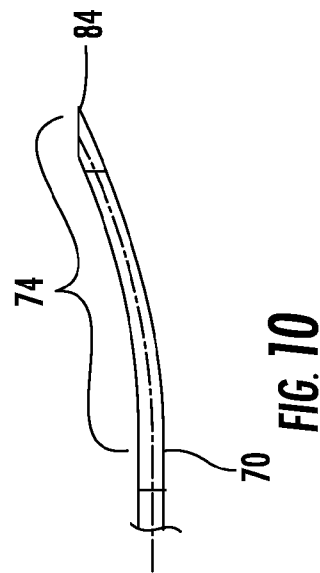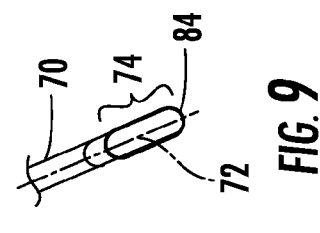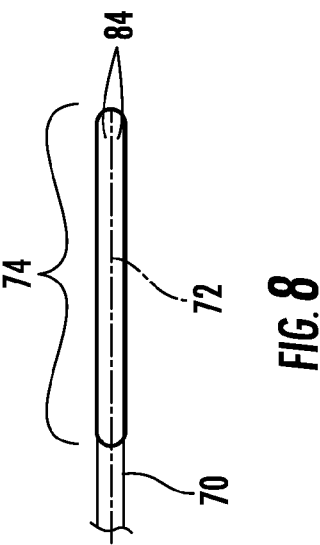

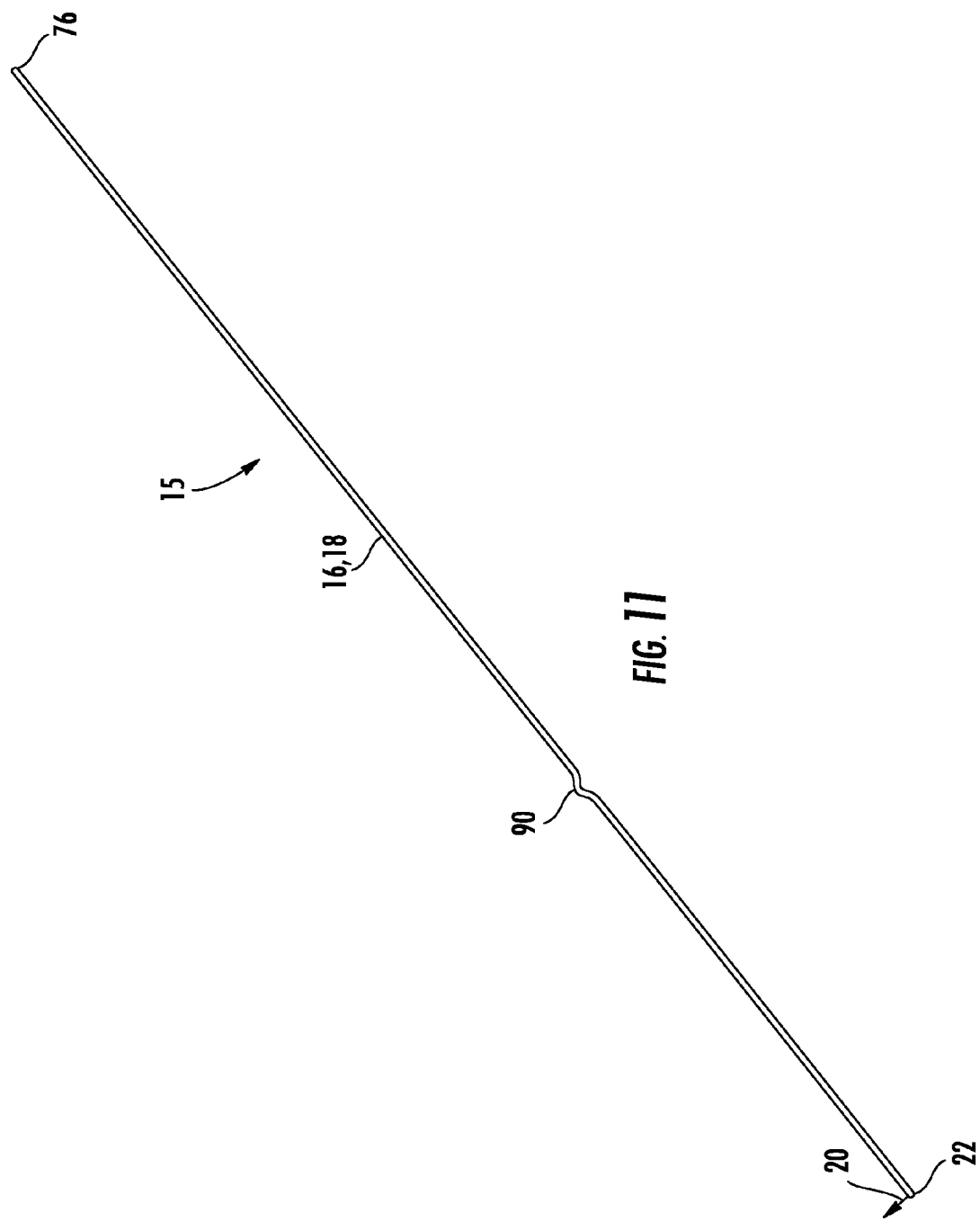

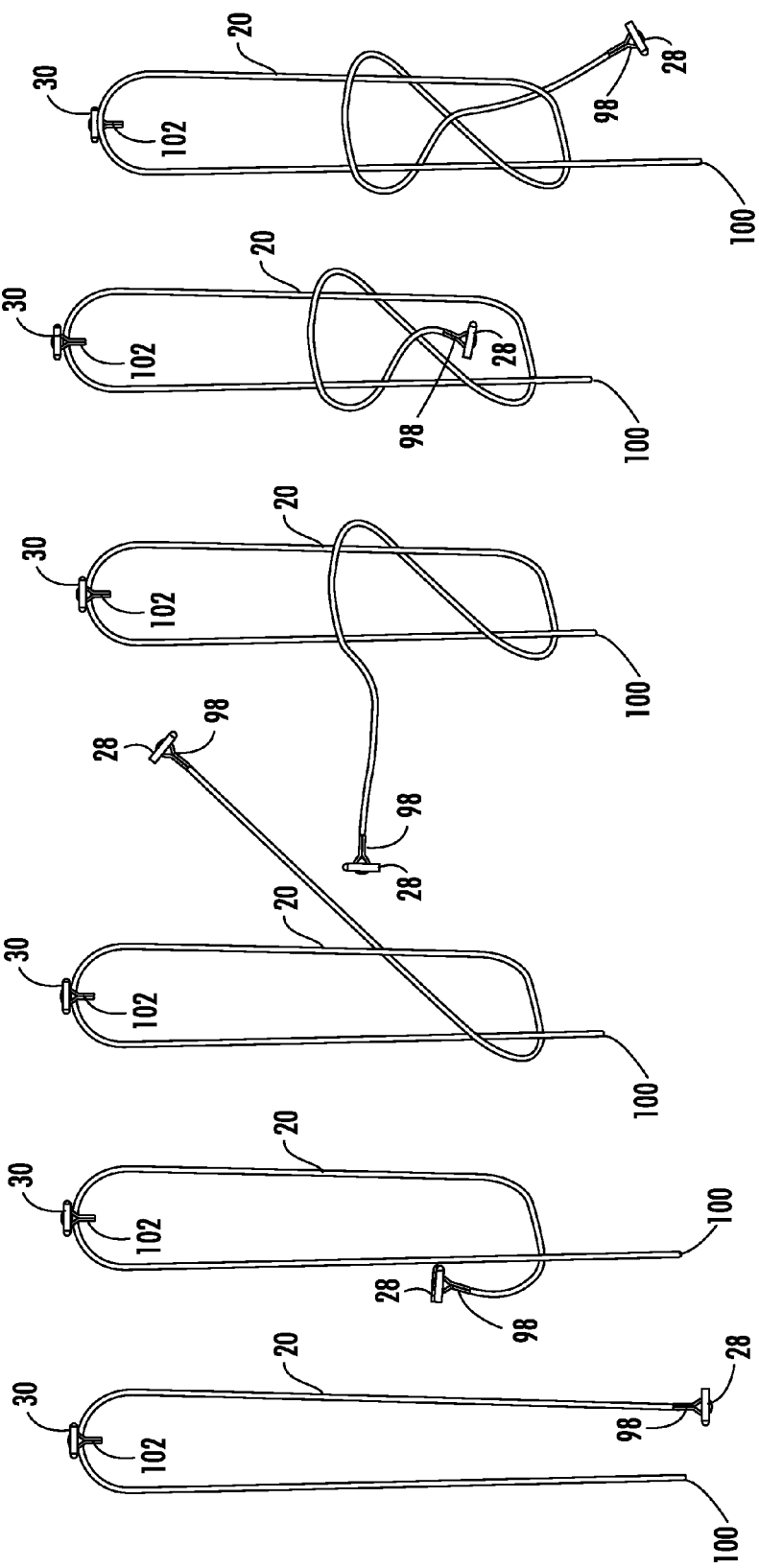

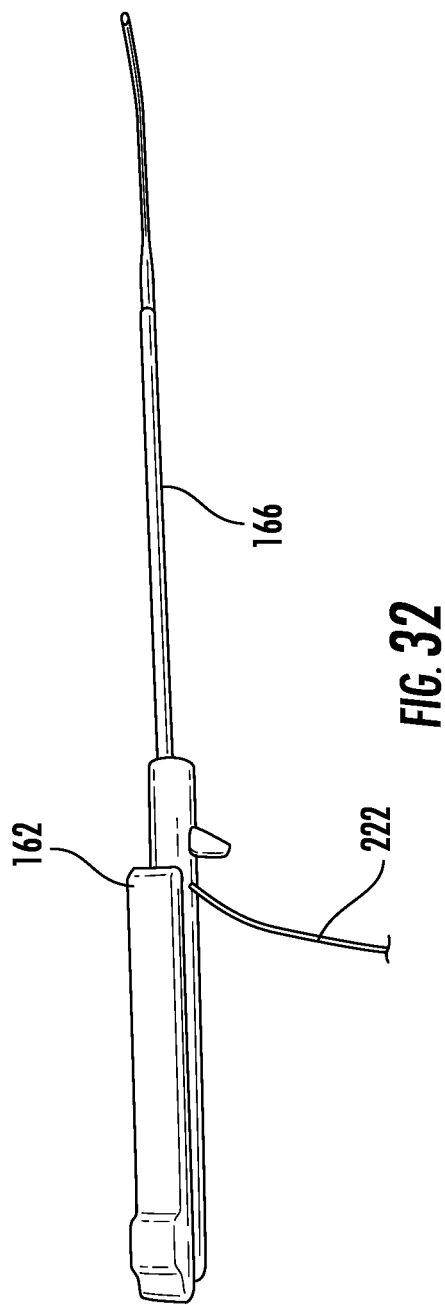

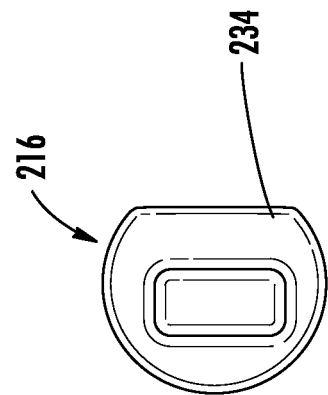
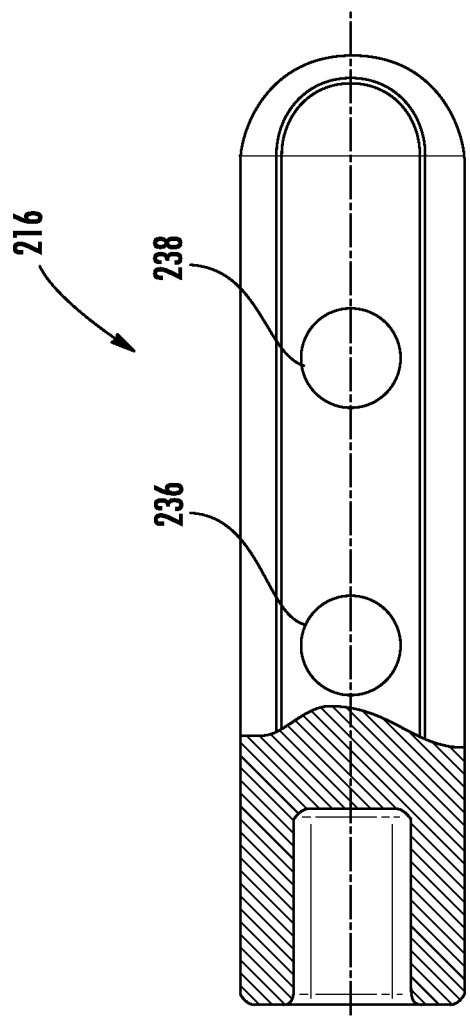

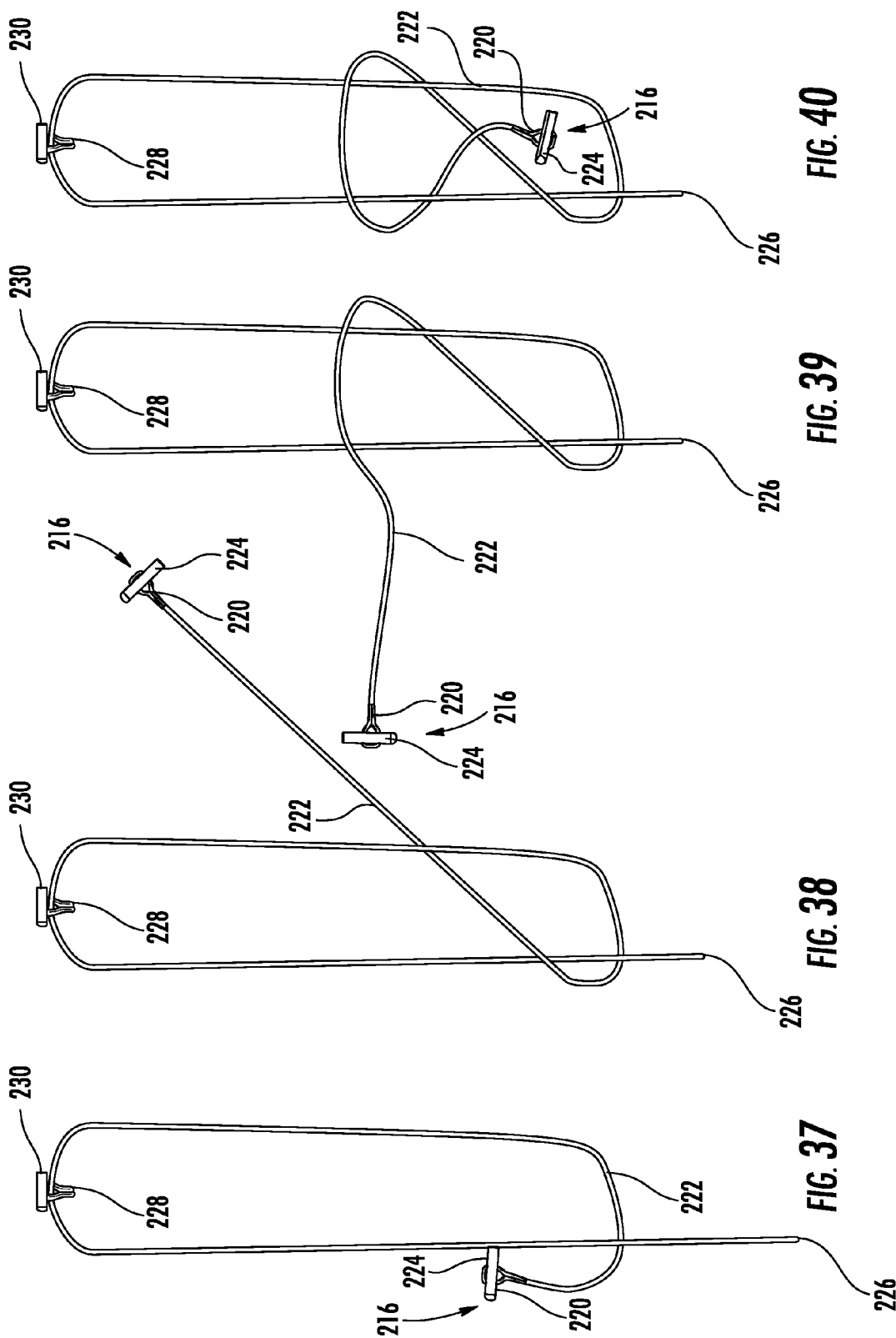

DRIVE SYSTEM FOR TISSUE REPAIR

CROSS-REFERENCE TO RELATED APPLICATION

This application claims the benefit of U.S. provisional patent application Ser. No. 61/580,024, filed on Dec. 23, 2011.

FIELD OF THE INVENTION

The invention relates to suture insertion drive systems usable in arthroscopy, and more particularly, to suture insertion drive systems configured to advance one or more drive shafts through a tissue to install a suture therein.

BACKGROUND

There have been numerous advances in surgical techniques to repair orthopedic injuries. Arthroscopic surgery that at one time caused patients months of incapacitation and recuperation can now be accomplished with surgical procedures that are minimally invasive and foster fast patient recoveries. Most tears are repaired using arthroscopic techniques, categorized as either "outside-in" or "inside-out." The inside-out technique requires that a surgeon place needles using arthroscopic visualization through both meniscal fragments and then out through the joint, exiting percutaneously. The needles pull sutures through the meniscal fragments and are used to stabilize a tear while it heals. The outside-in approach was developed to eliminate the large incision required in the inside-out method. In the outside-in procedure, a surgeon utilizes needles as in the inside-out technique. However, in this technique, safe passage of the needles is more easily controlled using knowledge of anatomical landmarks to avoid the peroneal nerve.

The outside-in procedure includes first directing a needle from a percutaneous arthroscopic accessory portal that is outside, and, then, directing the individual needles through the tissue on both sides of the meniscus tear. The surgeon is able to view inside via an arthroscope inserted through a viewing portal. Once the needles span the tear as seen through the arthroscope, a suture is positioned across the tear inside the knee using the two needles. After both needles exit the capsule, the needles are cut from the suture and an interference knot is tied on the suture and is formed from several knots tied onto a knot such that the resulting knot is large enough to prevent the interference knot from being pulled from the opening in the tissue made by the needle. When the needles are removed, the suture is left in place, and the interference knot is pulled back into the knee through the suturing portal until the knot is positioned against the tear site. The process is then repeated several times until the tear is stabilized. The procedure is completed by tying all of the suture tails together through an incision under the skin outside of the knee joint.

Both techniques focus on placement of sutures that bring two surfaces of the torn meniscus together so that healing may occur. Tying knots in sutures while operating in the extremely confined environment provided by the hollow needles is very difficult and requires incredible dexterity. Indeed, a substantial portion of the time required for the procedure is due to the time that it takes to place the sutures. While there exist numerous systems for facilitating the inside-out techniques and numerous systems for facilitating the outside-in technique, there exists a need for more efficient implementation techniques.

SUMMARY OF THE INVENTION

A suture drive system configured to assist in attaching a suture to tissue within a patient, and in at least one application, repairing meniscal tears and shoulder tissue tears is disclosed. The suture drive system may be interchangeable in that the system can be adapted to insert different suture systems into tissue of a patient. In particular, in one embodiment configured to employ an inside-out suture delivery method, the suture drive system may advance two combinations of push rods and two swaged needles having one or more sutures attached thereto. In another embodiment configured to employ an outside-in suture delivery method, the suture drive system may advance two combinations of push rods and drive shafts to deliver two anchors releasably affixed to the distal ends of the drive shafts into tissue to close an opening in the tissue.

In at least one embodiment, the suture drive system may be useful for repairing tears in soft tissue and may be formed from a dual drive system configured to advance two combinations of drive shafts and push rods, one combination at a time. In addition, the suture drive system may be interchangeable in that the system can be adapted to insert different suture systems into a tissue. In particular, in one embodiment configured to employ an inside-out suture delivery method, the suture drive system may advance two combinations of push rods and drive shafts, which are two swaged needles having a suture attached to a proximal end of the needles. In another embodiment configured to employ an outside-in suture delivery method, the suture drive system may advance two combinations of two push rods and two drive shafts that are attached thereto to deliver two anchors releasably affixed to the distal ends of the drive shafts into tissue to close an opening in the tissue.

In another embodiment, the suture drive system may be formed from a drive body supporting a drive actuator and drive mechanism that may be used to separately drive push rods positioned within the drive body together. The drive mechanism may be formed from one or more gears in communication with a first linear gear forming a rack and pinion drive mechanism. In particular, the drive actuator may include a second linear gear configured to engage the gear, which is in turn configured to engage the first linear gear. The first linear gear may be positionable via a push rod selector to advance one of two push rods within a cannula. The push rod selector may have at least a portion extending outside of the drive body. The second linear gear may be positioned on a proximal end of the drive actuator in close proximity to the drive mechanism. The first linear gear may include teeth in contact with teeth extending from the bottom of the gear, and the second linear gear may include teeth in contact with teeth extending from the top of the gear. In another embodiment, the gear may be formed from a first gear in contact with the first linear gear and a second gear in contact with the second linear gear. The first gear may be rigidly coupled to the second gear, and the first gear may be larger than the second gear. As such, a mechanical advantage can be created such that they first linear gear may travel further than the linear travel of the second linear gear. In one embodiment, a trigger coupled to the drive actuator may be advanced one unit of measurement, while the a cannula to which the drive mechanism is attached is advanced linearly more than the one unit of measurement due to the mechanical advantage.

An advantage of the suture drive system is that the system enables a surgeon to choose between using the inside-out suture system or outside-in suture system and use the same device for both techniques.

Another advantage of the suture drive system is that the system may be packaged in a loaded state such that when the system is removed from packaging, it is ready for use.

Yet another advantage of the suture drive system is that the system may be disposable.

Another advantage of the suture drive system is that the system may include a push rod selector component that enables a surgeon to choose which needle or suture anchor to deploy first.

Still another advantage of the suture drive system is that the system uses a single trigger for ease of use by a surgeon.

Another advantage of the suture drive system is that the system includes a preloaded cartridge that may be quickly and easily inserted into a drive body depending on whether a needle with attached suture or an anchor is to be deployed.

These and other embodiments are described in more detail below.

BRIEF DESCRIPTION OF THE FIGURES

The accompanying drawings, which are incorporated in and form a part of the specification, illustrate embodiments of the presently disclosed invention and, together with the description, disclose the principles of the invention.

FIG. 5 is a top view of a cannula of the suture drive system.

FIG. 6 is a right side view of a cannula of the suture drive system.

FIG. 7 is a cross-sectional view of a cannula of the suture drive system taken along section line 7-7 in FIG. 5.

FIG. 8 is a cross-sectional view of the distal window of the cannula taken at section line 8-8 in FIG. 7.

FIG. 9 is a cross-sectional view taken at section line 9-9 in FIG. 7.

FIG. 10 is a detail view of the distal window of the cannula shown in FIG. 7.

FIG. 11 is a side view of a needle of the suture drive system.

FIGS. 20-26 is a series of side views showing the formation of a figure eight knot usable in the suture drive system with the outside-in suture method.

FIG. 32 is a side view of the push rod guide support housing of FIG. 31 with a cannula extending distally therefrom.

FIG. 33 is a front view of an anchor usable with the system shown in FIG. 29.

FIG. 34 is a left side view of the anchor shown in FIG. 33.

FIG. 37-41 is a series of side views showing the formation of a figure eight knot usable in the suture drive system of FIG. 29 with the outside-in suture method.

DETAILED DESCRIPTION OF THE FIGURES

Figure 1:
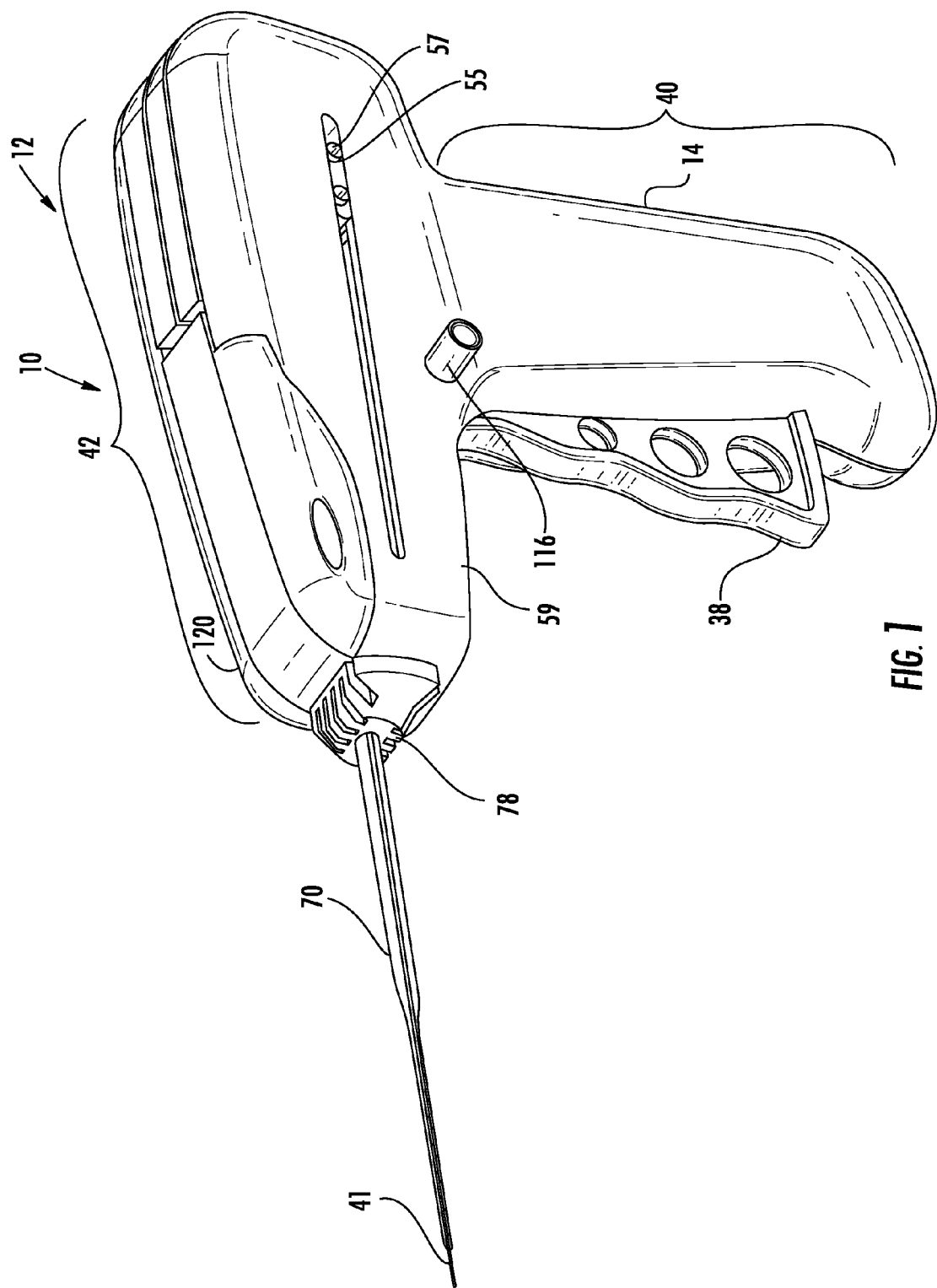
FIG. 1 is a perspective view of the suture drive system.

As shown in FIGS. 1-47, this invention is directed to a suture drive system 10 configured to assist in attaching a suture to tissue, such as, but not limited to, tissue within a patient. In at least one embodiment, the suture drive system 10 may be useful for repairing tears in soft tissue, such as, but not limited to, repairing meniscal tears and shoulder tissue tears. The suture drive system 10 may be formed from a dual drive system 12 configured to advance two combinations of drive shafts 15 and push rods 24, 26, one combination at a time. In addition, the suture drive system 10 may be interchangeable in that the system 10 can be adapted to insert different suture systems into a tissue. In particular, in one embodiment configured to employ an inside-out suture delivery method, the suture drive system 10 may advance two combinations of push rods 24, 26 and drive shafts 15, which are two swaged needles 16, 18 having a suture 20 attached to a proximal end 22 of the needles 16, 18. In another embodiment configured to employ an outside-in suture delivery method, the suture drive system 10 may advance two combinations of two push rods 24, 26 and two drive shafts 15 that are attached thereto to deliver two anchors 28, 30 releasably affixed to the distal ends of the drive shafts 15 into tissue to close an opening in the tissue.

As shown in FIGS. 1-4, the dual drive system 12 may include a dual drive body 14 supporting at least a first drive actuator 34 and a second drive actuator 36. In one embodiment, the dual drive body 14 may be configured to include a handle 40 extending from a drive region 42. The dual drive body 14 may be formed from two halves coupled together with at least one connector 114. The handle 40 may be non-parallel with the drive region 42, and, in at least one embodiment, may be generally orthogonal to the drive region 42. One or more triggers 38 may be configured to actuate the first and second drive actuators 34, 36. The trigger 38 may extend through a trigger opening 44 in an outer surface of the handle 40 upon which fingers of a user rest. The trigger 38 may be biased away from the first and second drive actuators 34, 36. In at least one embodiment, the trigger 38 may be biased with one or more springs 118 or other appropriate device. The trigger 38 may include an alignment arm 116 extending outwardly from both sides of the dual drive body 14 such that the trigger 38 is movable relative to the dual drive body 14 from outside the dual drive body 14, thereby allowing the trigger 38 to be moved between the first and second drive actuators 34, 36. A click spring 118 may limit movement of the trigger 38 between first and second drive actuators 34, 36. In one embodiment, the click spring 118 may be formed from a V-shaped spring.

The first drive actuator 34 may be formed from a lever arm 46 having a first end 48 that is configured to bear against the trigger 38 and a second end 50 that pivotably supports a connect arm 52. An opposite end of the connect arm 52 may be pivotably coupled to a slide 54. The first drive actuator 34 may have an offset pivot point 56 such that a distance between the pivot point 56 and the first end 48 is less than a distance between the pivot point 56 and the second end 50. In at least one embodiment, the distance between the pivot point 56 and the second end 50 is at least three times more than the distance between the pivot point 56 and the first end 48.

The slide 54 may be pivotably attached to the connect arm 52 of the first drive actuator 34 and contained within the push rod support channel 64. The slide 54 may include one or more slots 60 for receiving a push rod hub 58 of a drive shaft 15. The slot 60 may be a dovetail slot that limits movement of the push rod hub 58 of the push rods 24, 26 that is not aligned with a longitudinal axis 62 of the push rod support channel 64. In at least one embodiment, the suture drive system 10 may include a slide 54 for each push rod 24, 26. The slide 54 may be aligned to push rod support channel 64 with posts 55 extending outwardly. The alignment posts 55 may include a head 57 contained within a slot 59 that is generally aligned with the push rod support channel 64.

The dual drive body 14 may include one or more cannula support chambers 66 positioned with the drive region 42. One or more push rod support channels 64 may be in communication with the cannula support chamber 66. The dual drive body 14 may include a push rod support channel access opening 68 that provides access to the push rod support channel 64 and the cannula support chamber 66. As shown in FIGS. 1-4, the suture drive system 10 may include a hatch lid 120 for removably covering the push rod support channel access opening 68.

Figure 2:
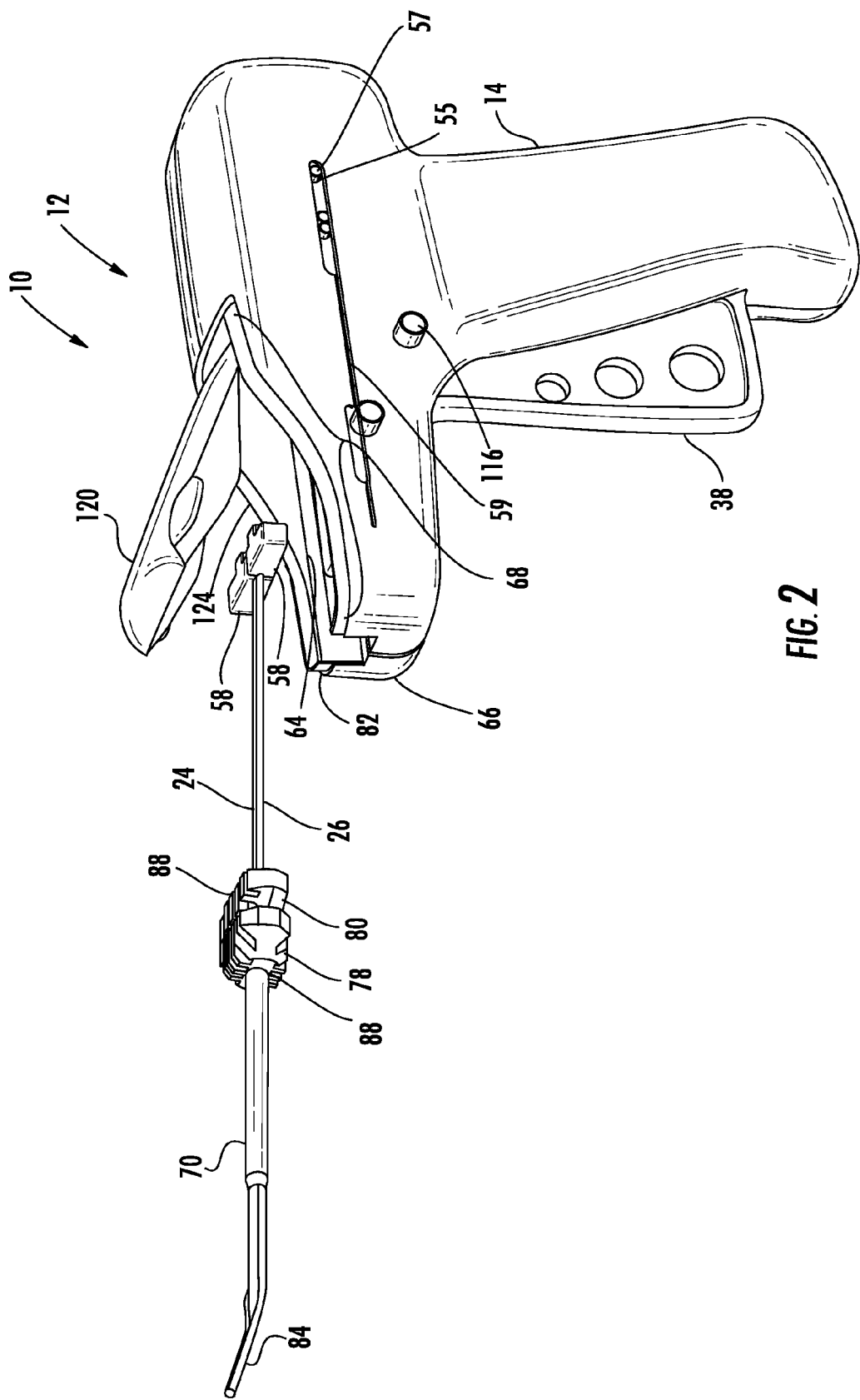
FIG. 2 is a partially disassembled perspective view of the suture drive system.
Figure 3:
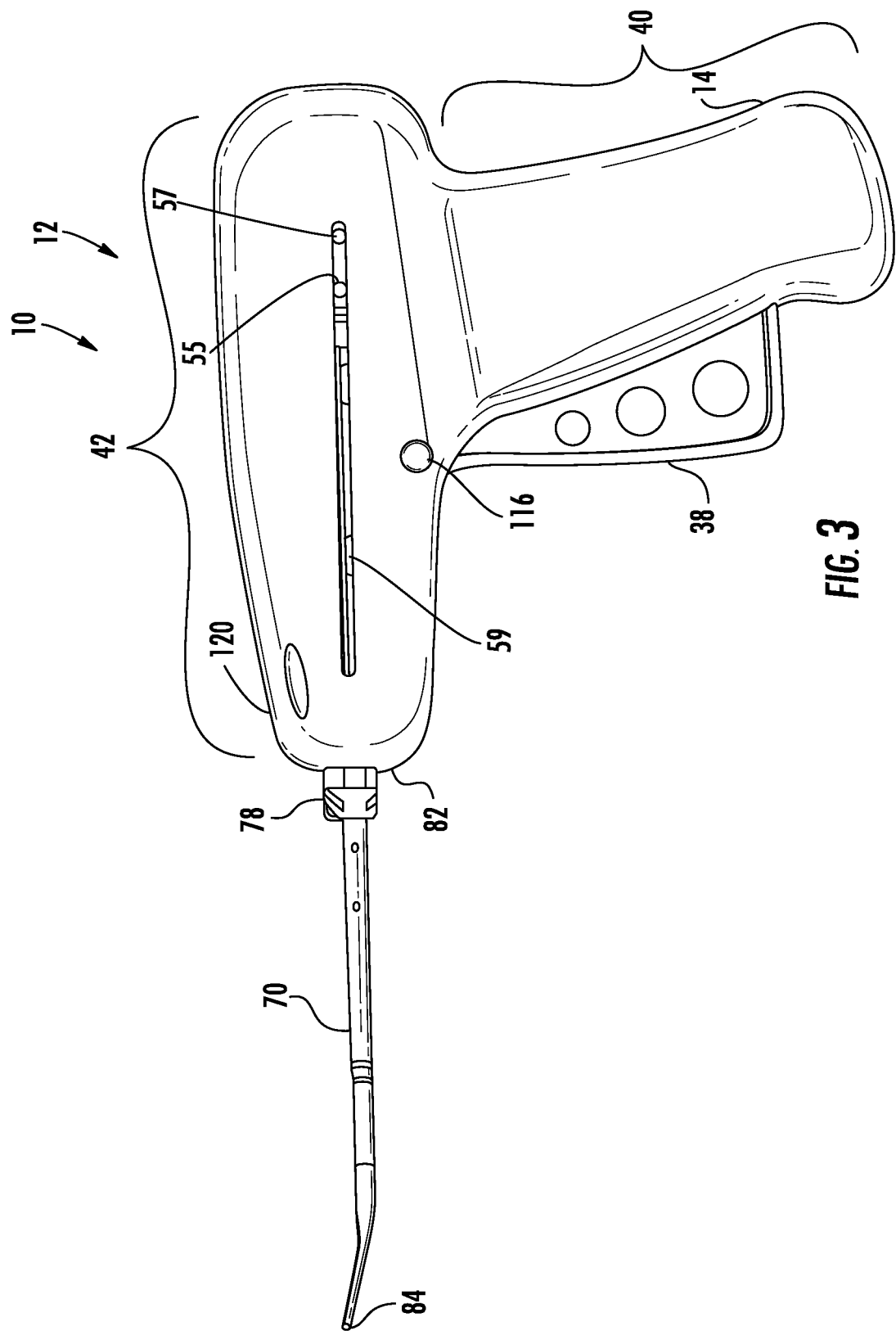
FIG. 3 is a side view of the suture drive system of FIG. 1.
Figure 4:
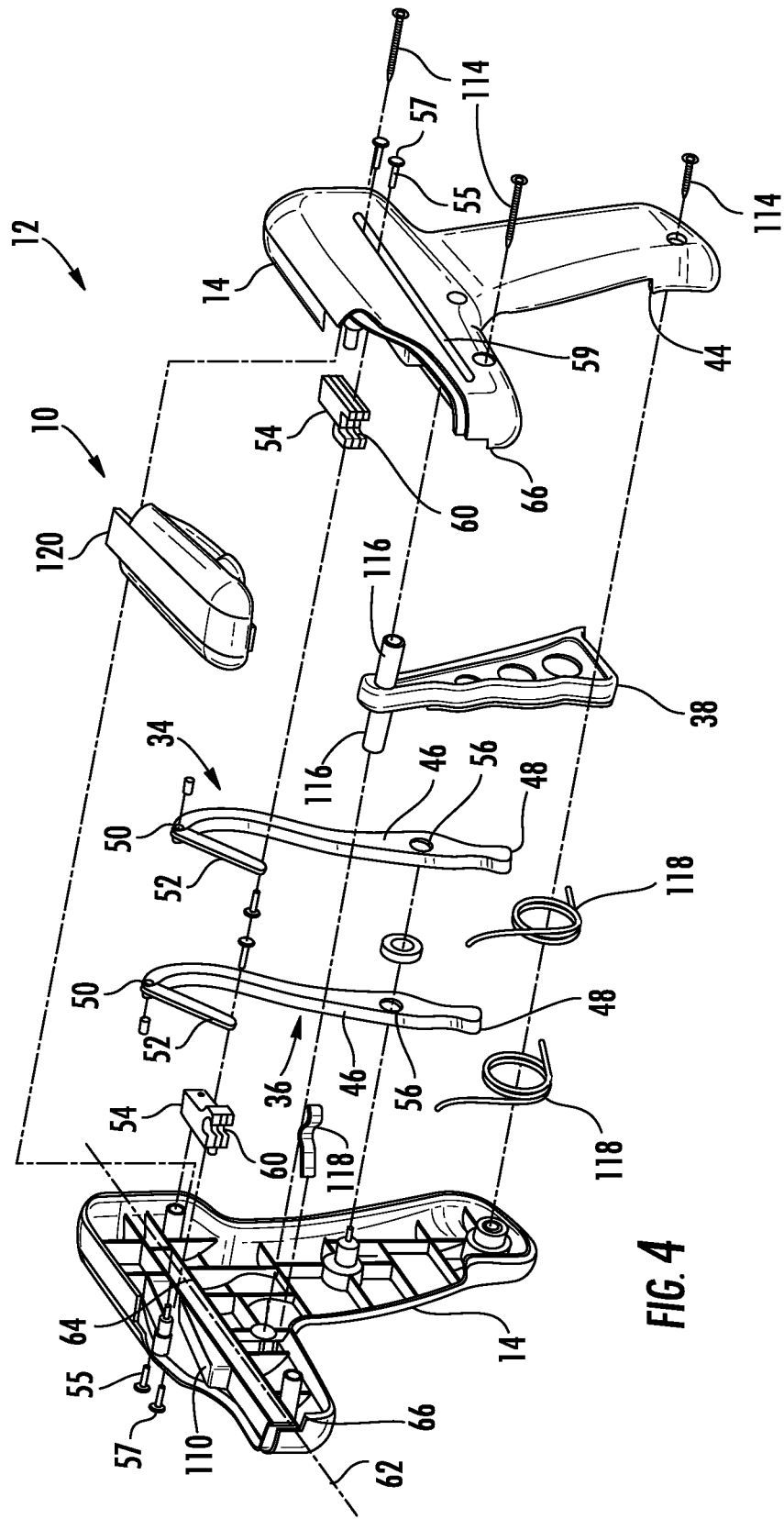
FIG. 4 is an exploded perspective view of the suture drive system.
Figure 12:
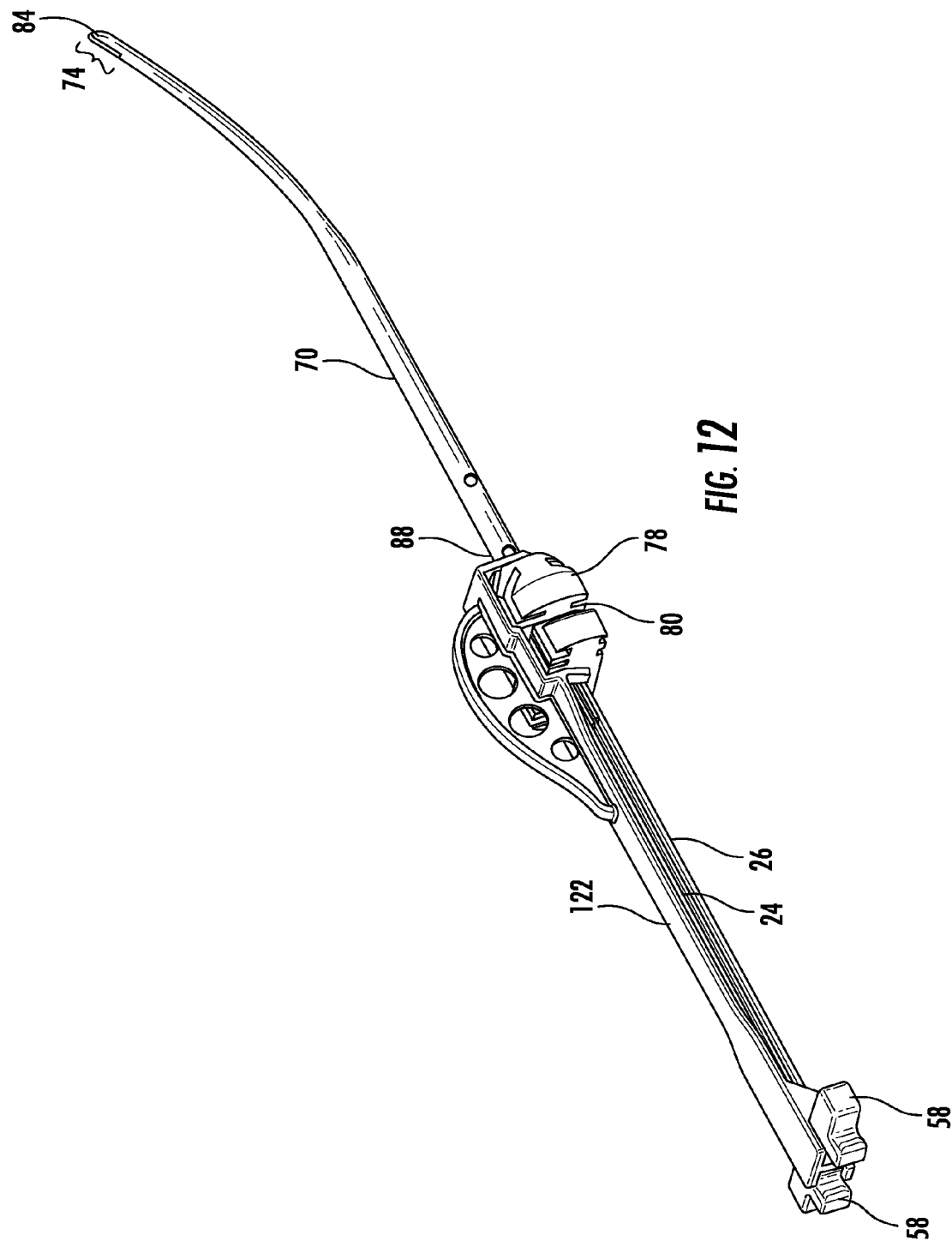
FIG. 12 is a perspective view of a cannula with drive shafts, which are needles, installed therein and held in place with a cartridge.

As shown in FIGS. 5-10, the suture drive system 10 may include one or more cannulas 70 having an inner channel 72 configured to receive one or more drive shafts 15. In one embodiment, one or more cannulas 70 may be provided. The cannulas 70 may be configured to be releasably attached to the dual drive body 14. A cannula base 78 may be attachable to the dual drive body 14 in the cannula support chamber 66, as shown in FIGS. 1-3. The cannula base 78 may include one or more grooves 80, as shown in FIG. 2, configured to receive an end wall 82 forming a distal end of the dual drive body 14. The groove 80 attached to the end wall 82 prevents the cannula 70 from moving laterally, axially and rotationally. In one embodiment used for the inside-out suture delivery method, the cannula 70 may include a blunt tip. In another embodiment used for the outside-in suture delivery method, the cannula 70 may include a pointed tip for piercing tissue and delivering the anchors 28, 30.

In one embodiment, as shown in FIGS. 6-10, the cannula 70 may include an inner channel 72 configured to receive one or more drive shafts 15 coupled to at least one push rod 24, 26. In this embodiment, the drive shafts may be needles 16, 18 that are partially contained within hollow push rods 24, 26. The inner channel 72 of the cannula 70 may be configured to receive at least a portion of two needles 16, 18 simultaneously within at least a portion of the cannula 70 and may have a distal window 74 through which distal ends 76 of the needles 16, 18 extend. The cannula 70 may be straight, may be curved between about 15 degrees and about 30 degrees to the left, may be curved between about 15 degrees and about 30 degrees to the right, or have another appropriate position. The cannula 70 may include one or more tag orifices 86 through which the tag ends of the sutures 20 may extend.

The needles 16, 18 may be swaged needles having a suture 20 attached to a proximal end 22 of the needles 16, 18. Two swaged needles 16, 18 may be contained within the cannula 70 such that a distal tip 76 of each of the swaged needles 16, 18 may be slightly proximal of a distal end 84 of the cannula 70 and proximal ends 22 of the swaged needles 16, 18 may extend proximally from a proximal end 88 of cannula 70. The push rods 24, 26 may be hollow and contain the proximal ends 22 of the needles 16, 18, such that the proximal ends 22 contact the push rod hubs 58. One or both of the swaged needles 16, 18 may include a crimp 90, as shown in FIG. 11, that forms an interference fit with a crimped section 92 of the push rods 24, 26, as shown in FIG. 27, which may be, but is not limited to being, positioned at the distal end 96 of the push rods 24, 26.

Figure 27:
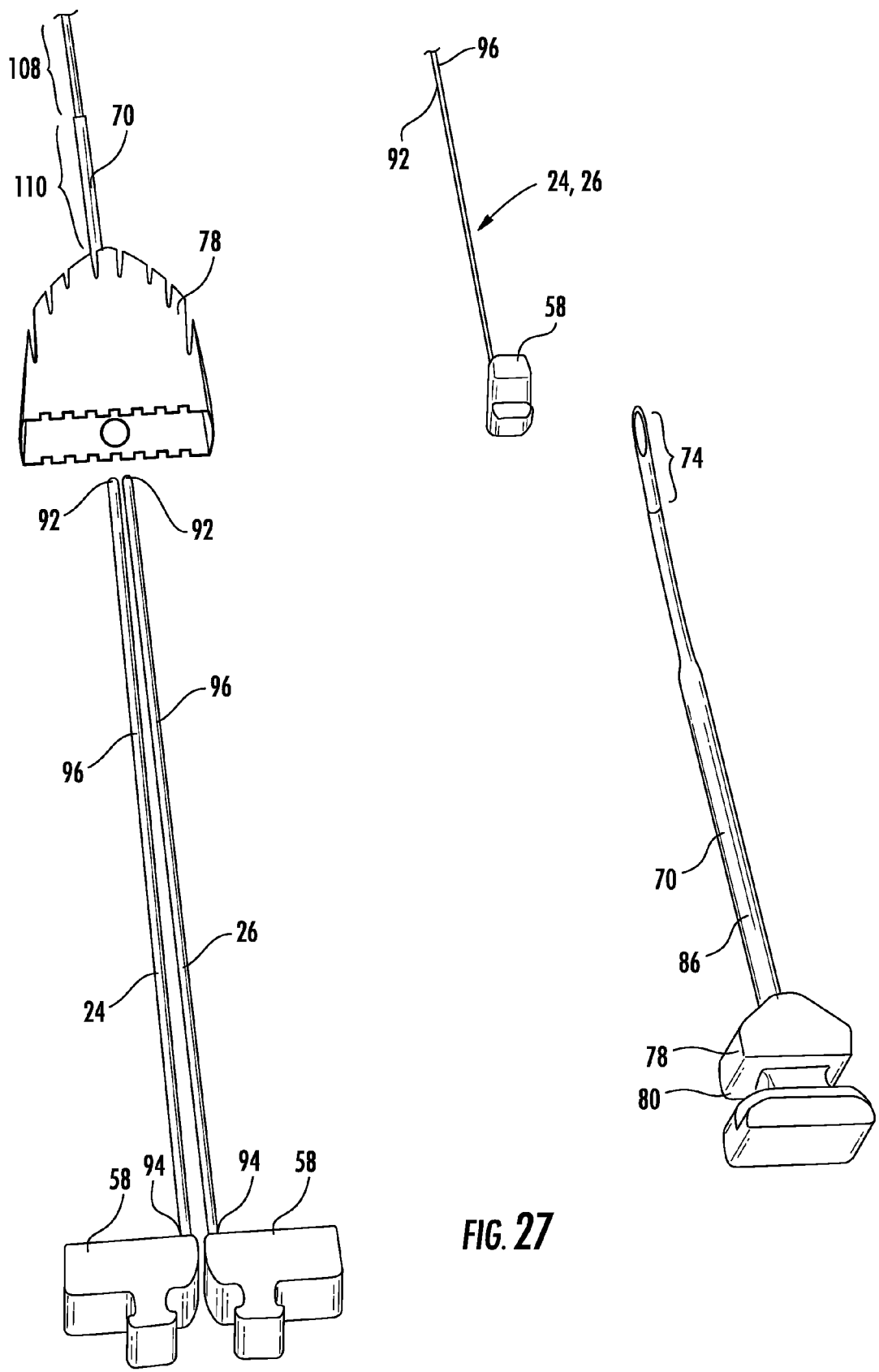
FIG. 27 is a perspective view of drive shafts coupled to push rods that are positioned to be installed into cannulas.
Figure 28:
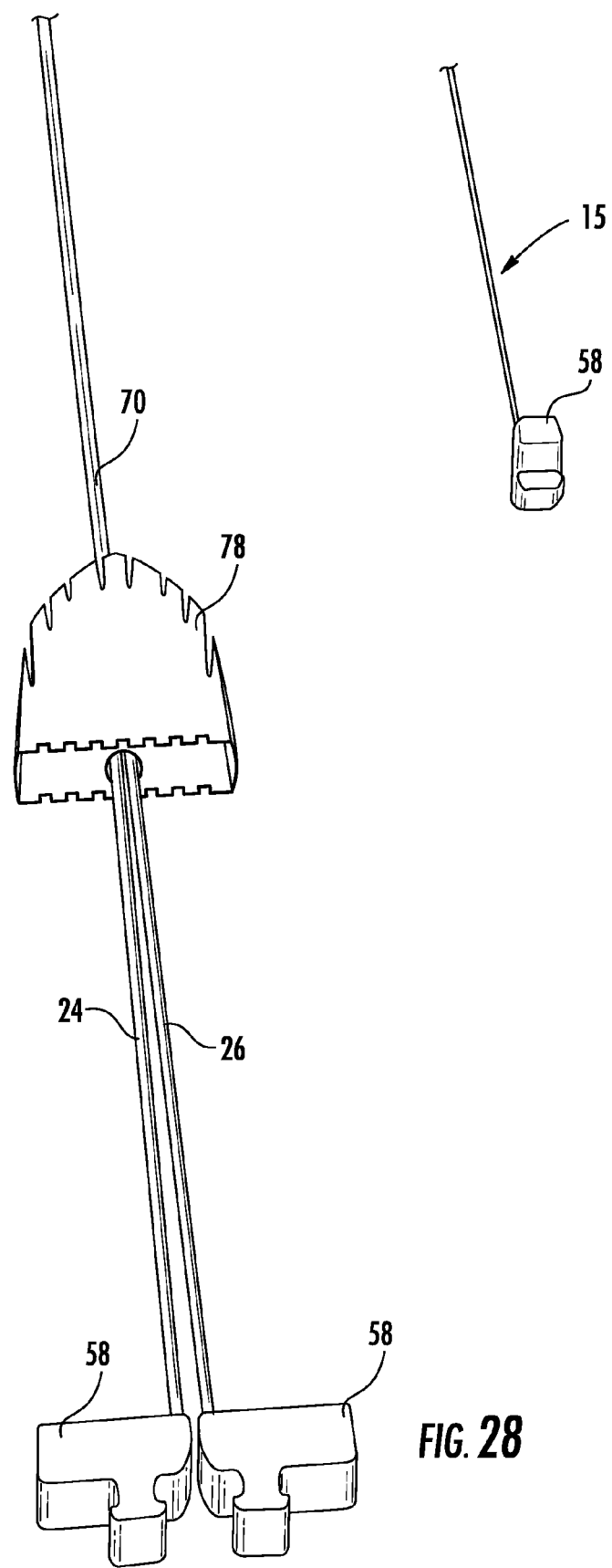
FIG. 28 is a perspective view of push rods being inserted into cannulas.

In another embodiment, as shown in FIGS. 27-28, in which the suture drive system 10 is configured to implement the outside-in suture method, a drive shaft 15 may be coupled to each of two push rods 24, 26. The drive shafts 15 have smaller diameters than the push rods 24, 26 and, are generally aligned along a single longitudinal axis in series. The drive shafts 15 may be affixed to the distal ends 96 of the push rods 24, 26. The push rods 24, 26 may include push rod hubs 58 on a proximal end 94. In such an embodiment, the cannula 70 may be formed from a distal section 108 and a proximal section 110. The proximal section 110 may contain both push rods 24, 26 simultaneously, but to prevent inadvertent actuation of both push rods 24, 26, the only one rod 24, 26 at a time may fit in the distal section 108. Thus, only a portion of cannula 70 may be configured to house a portion of two push rods 24, 26 simultaneously.

Figure 18:
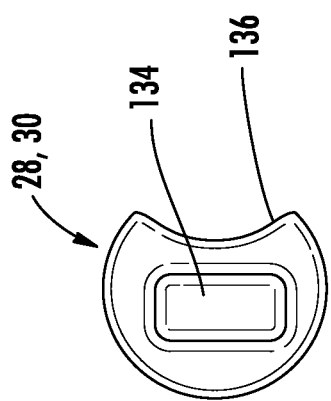
FIG. 18 is a left side view of the anchor of FIG. 17.
Figure 17:
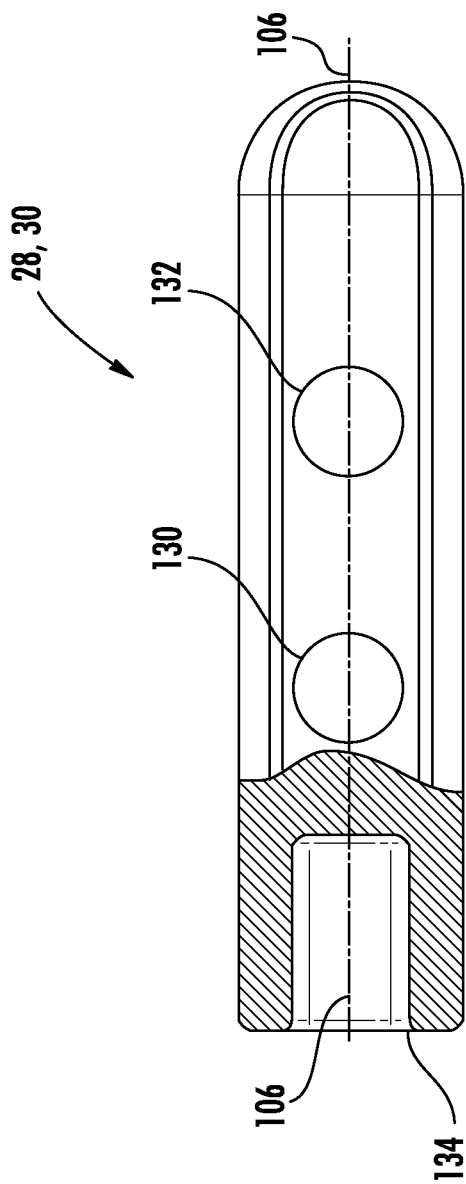
FIG. 17 is a front view of an anchor of the suture drive system and includes a partial cross-section.
Figure 19:
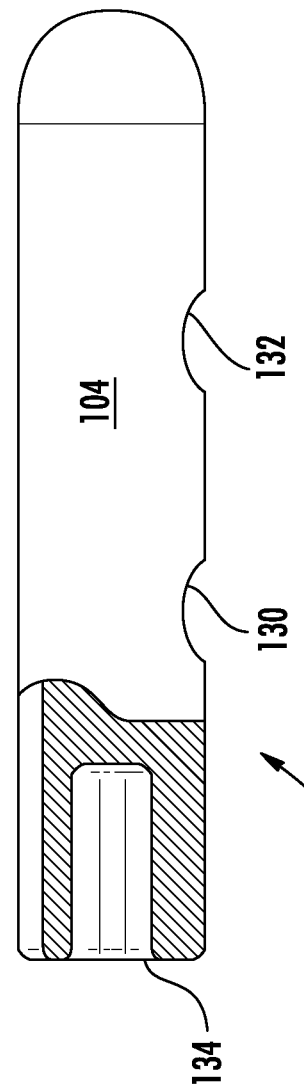
FIG. 19 is a bottom view of the anchor and includes a partial cross-section.
Figure 26:
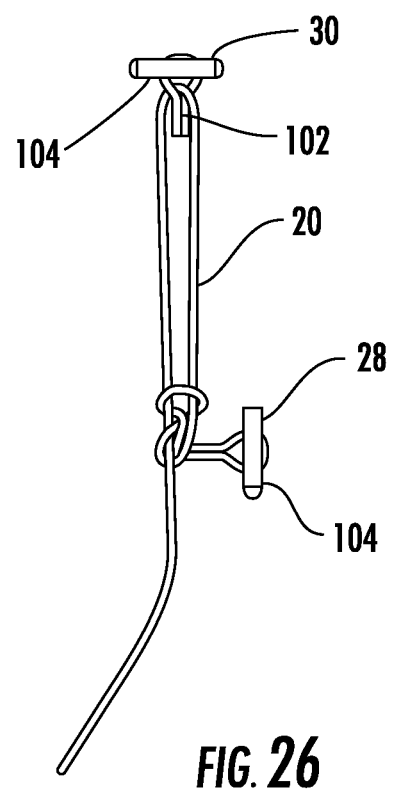

The drive shafts 15 may include one or more anchors 28, 30 releasably affixed to a distal end 96 of each of the drive shafts 15. The anchors 28, 30, as shown in FIGS. 17-19, may be elongated members and may be formed from a biocompatible material, such as, but not limited to, PEEK. The anchors 28, 30 may include first and second orifices 130, 132 extending through an outer surface 104 and generally orthogonal to a longitudinal axis 106 of the elongated member. The anchors 28, 30 may include a push rod receiving chamber 134 that may be aligned with the longitudinal axis 106. During use, a tip of a drive shaft 15 may be inserted into the push rod receiving chamber 134. The anchors 28, 30 may include a divot 136 in which the suture 20 extending between the first and second orifices 130, 132 may reside. Other embodiments may not include a divot 136.

As shown in FIGS. 20-26, a first end 98 of the suture 20 may be secured to a first anchor 28, and a second end 100 of the suture 20 may extend through a loop 102 attached to a second anchor 30. The second anchor 30 may be an elongated member, and the loop 102 may pierce the second anchor 30 twice through an outer surface 104 and generally orthogonal to a longitudinal axis 106 of the elongated member. The first end 98 of the suture 20, after extending through the loop 102 in the second anchor 30, forms a slip knot. In particular, the first end 98 of the suture 20, after extending through the loop 102 in the second anchor 30, may form a figure eight knot.

As previously set forth, suture drive system 10 may be configured to be an interchangeable system. As such, the suture drive system 10 may be configured to administer different suture systems to a patient. To assist in such endeavor, the suture drive system 10 may include one or more removable cartridges 122 configured to hold the drive shafts 15 and the push rods 24, 26 in the cannulas 70. In at least one embodiment, the cartridge 122 may be configured to hold the two needles 16, 18 and the push rods 24, 26 in the cannula 70 and keep the push rod hub 58 at a desired distance from the base 78 of the cannula 70. In another embodiment, the cartridge 122 may be configured to hold the two drive shafts 15 and the push rods 24, 26 in the cannula 70 and keep the push rod hub 58 at a desired distance from the base 78 of the cannula 70. The cartridge 122 may be formed from a unitary construction and may include first and second ends configured to be releasably attached to the push rod hub 58 and the base 78 of the cannula 70. The cartridge 122 may be formed from disposable materials, such as, but not limited to, plastics and metals.

The suture drive system 10 may also include a push rod hub guide ramp 124 having an push rod support channel access opening 68 for receiving a push rod hub 58 and guiding the push rod hub 58 into the slot 60 in the slide 54.

During use, the suture drive system 10 may be used to install a suture system into tissue, which may or may not be within a patient. Before installation of a suture 20 into the tissue, a user, such as a medical doctor, may choose which suture system to use. Such choice may be based upon personal preference, experience, location of the tear to be closed and other factors. The chosen suture system cartridge 122 may then be installed by opening the hatch lid 120, inserting the push rod hubs 58 into the push rod hub guide ramp 124, which guides the push rod hubs 58 into the slots 60 in the slides 54. Once secured therein, the cartridge 122 may be removed. In at least one embodiment, the slides 54 may be advanced at least minimally to prevent inadvertent release of the push rod hubs 58 from the slots 60, thereby enabling the dual drive system 12 to be turned at any orientation without risk of dislocation of the push rod hubs 58 from the slider 54.

Figure 13:
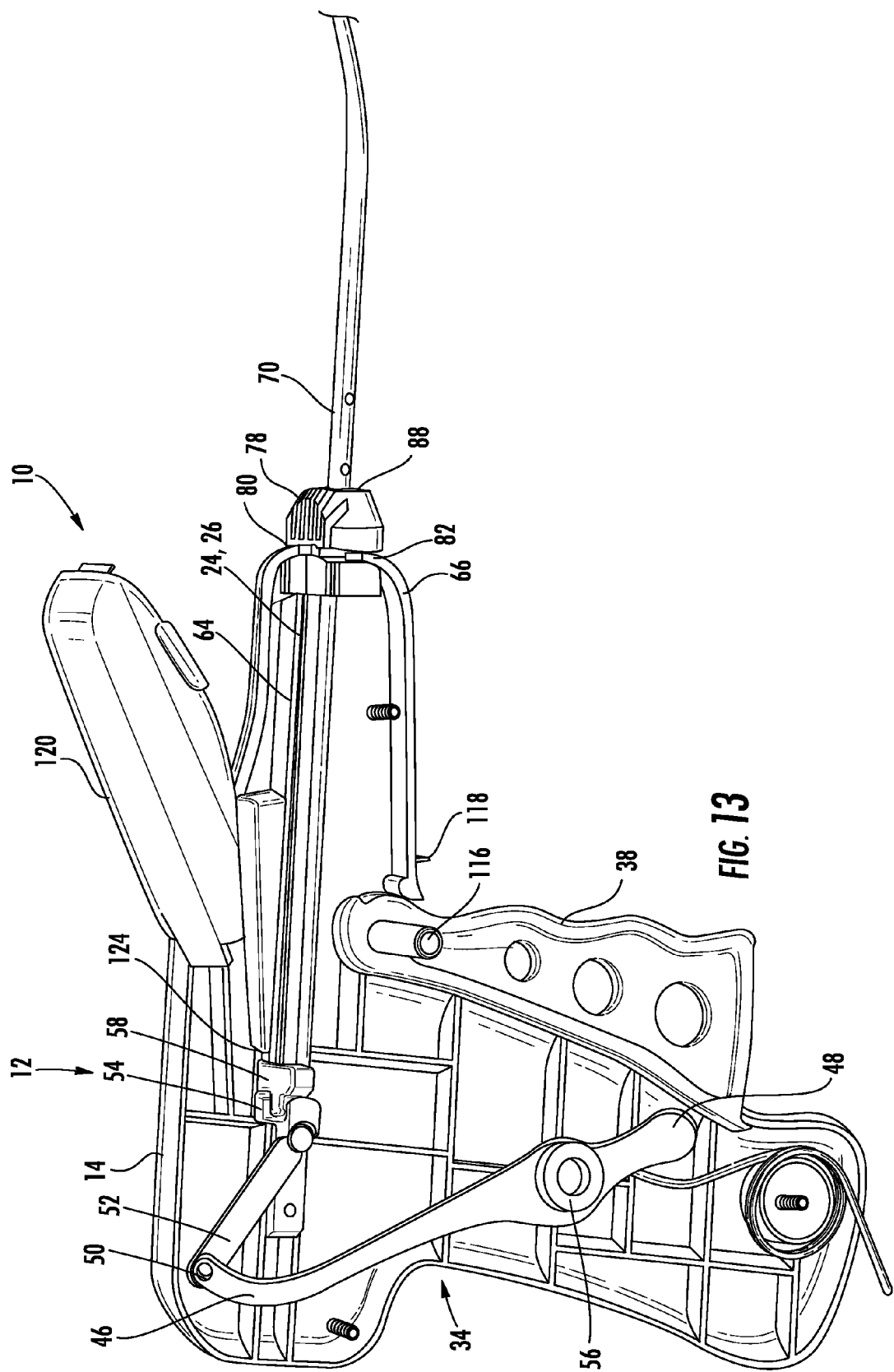
FIG. 13 is a cross-sectional view of the suture drive system in the start position.
Figure 14:
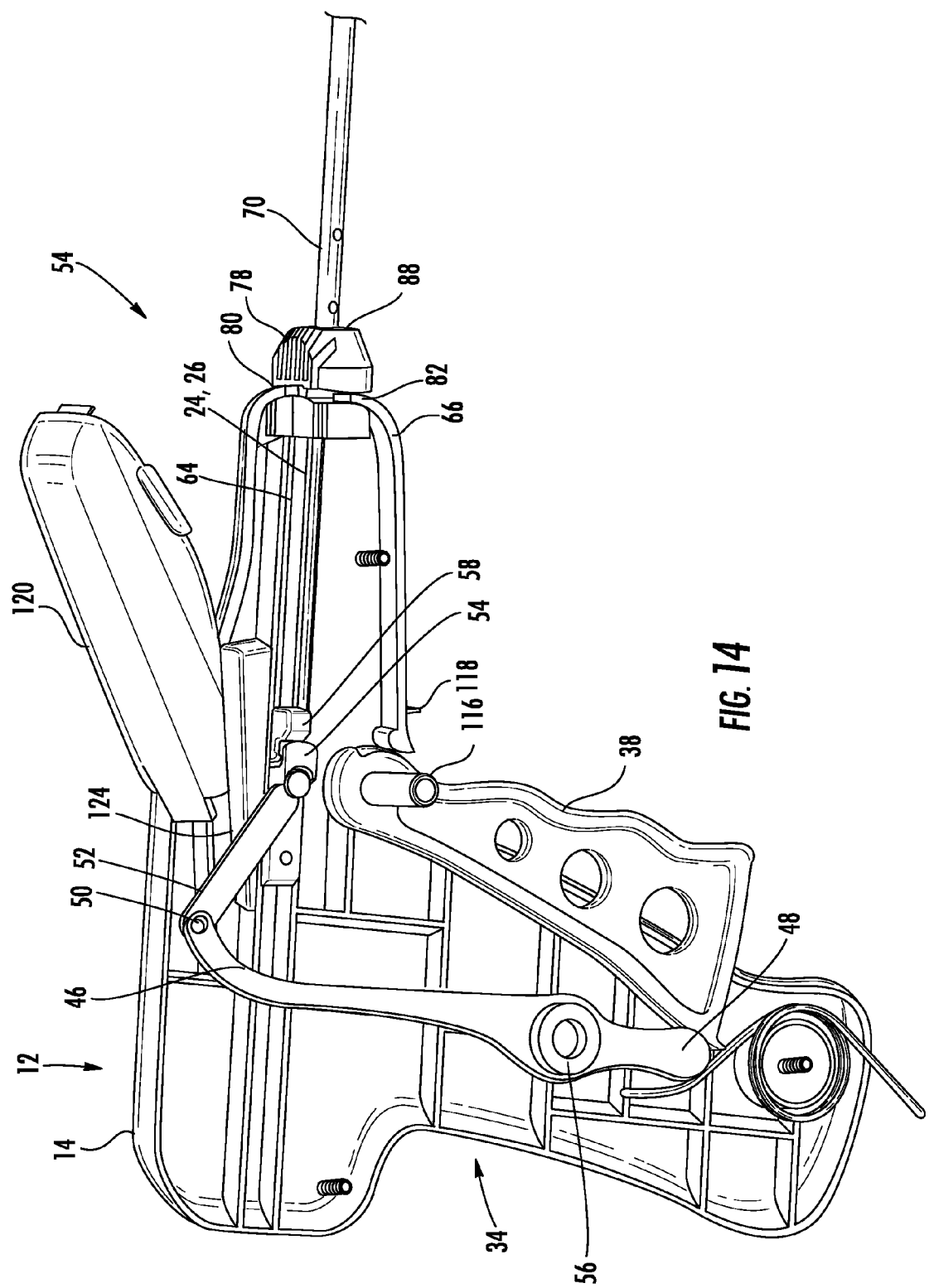
FIG. 14 is a cross-sectional view of the suture drive system with the trigger partially depressed.
Figure 15:
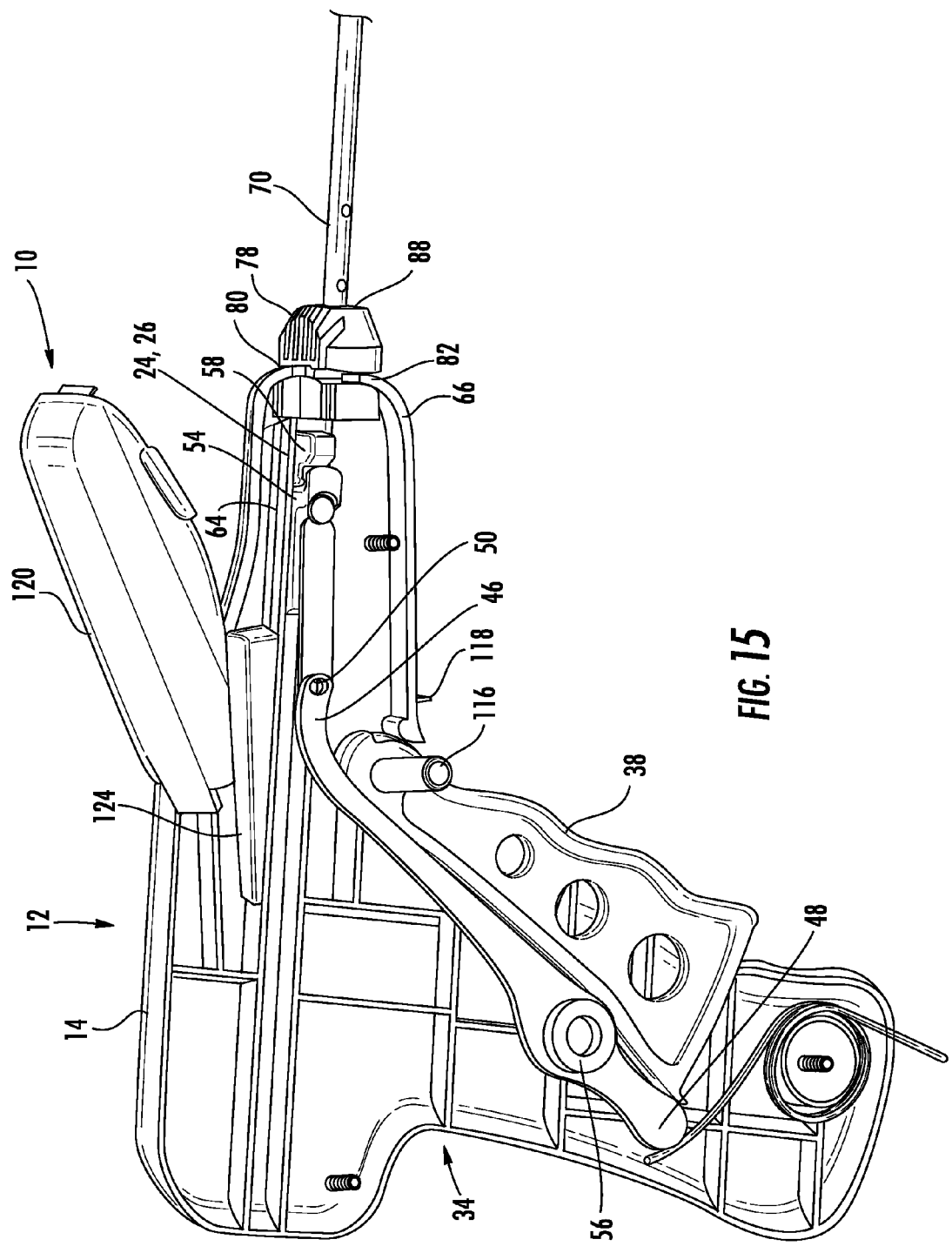
FIG. 15 is a cross-sectional view of the suture drive with the trigger fully depressed.
Figure 16:
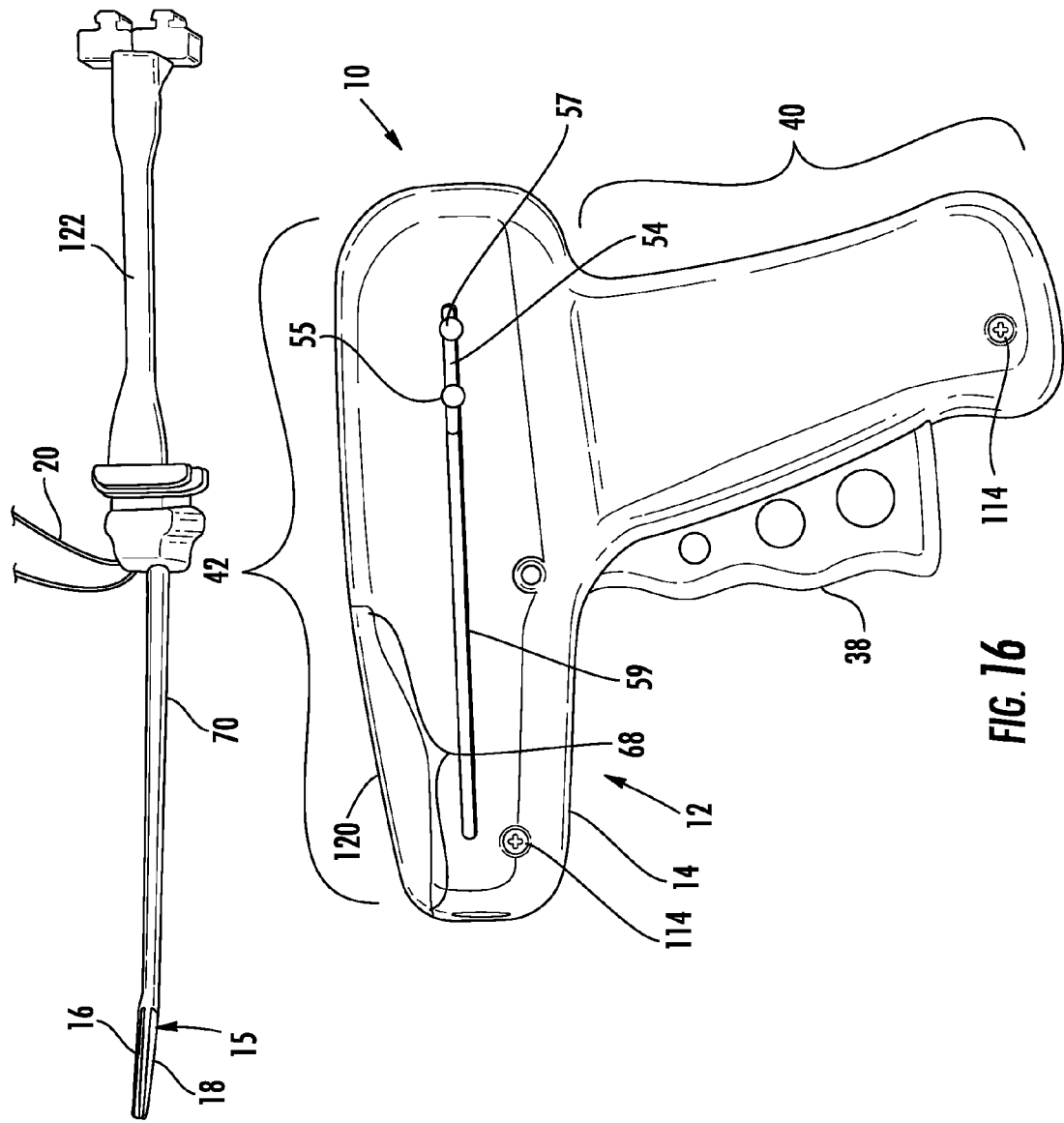
FIG. 16 is a side view of the suture drive system including a suture needle loaded cartridge coupled to first and second push rods each having a needle with suture secured thereto.

The distal tip 84 of the cannula 70 may then be inserted into incisions made in a patient until the tip 84 contacts the tissue in which the suture 30 is desired to be inserted. In embodiments in which the inside-out suture method is employed and the drive shafts 15 are needles 16, 18, the first drive actuator 34 may be activated by squeezing the trigger 38 towards the handle 40, as shown in FIGS. 13-15. Squeezing the handle causes one of the push rods 24, 26 and a needle 16, 18 contained therein to move into the tissue. More specifically, the trigger 38 bears on the first end 48 of the lever arm 46 of the first drive actuator 34, causing the lever arm to pivot about the pivot point 56. The second end 50 of the lever arm 46 is advanced generally toward the cannula 70. The lever arm 46 advances the connect arm 52 and the slide 54 attached thereto. The slide 54 in turn pushes the first needle 16 into the tissue. Once the trigger has been fully depressed, the first needle 16 is removed from the cannula 70. The alignment arm 116 is then pushed toward the handle 40 which causes the trigger 38 to be shifted from the first drive actuator 34 to the second drive actuator 36. The trigger 38 overcomes the resistance created by the click spring 118 and is moved into contact with the lever arm 46 of the second drive actuator 36. The trigger 38 may then be activated, and the second needle 18 advanced as described above. The second needle 18 may then be pulled from the cannula 70. After cutting the suture 20 from the needles 16, 18, the suture 20 may then be tied to the tissue to close a tear in the tissue.

Alternatively, in embodiments in which the outside-in suture method is employed, the cannula 70 may be inserted through the tissue before the trigger 38 is squeezed. The first drive actuator 34 may be activated by squeezing the trigger 38 towards the handle 40, as shown in FIGS. 13-15. The trigger 38 bears on the first end 48 of the lever arm 46 of the second drive actuator 34, causing the lever arm to pivot about the pivot point 56. The second end 50 of the lever arm 46 is advanced generally toward the cannula 70. The lever arm 46 advances the connect arm 52 and the slide 54 attached thereto. The slide 54 in turn pushes the drive shaft 15 attached to the first push rod 24 into the tissue. Once the trigger has been fully depressed, the first anchor 30 is deployed in the tissue and the first push rod 24 is withdrawn into the cannula 70. The alignment arm 116 is then pushed toward the handle 40 which causes the trigger 38 to be shifted from the first drive actuator 34 to the second drive actuator 36. The trigger 38 overcomes the resistance created by the click spring 118 and is moved into contact with the lever arm 46 of the second drive actuator 36. The trigger 38 may then be activated, and the second push rod 26 and drive shaft 15 attached thereto, advanced as described above. The second anchor 28 may then be installed in the tissue, and the push rod 26 may then be retracted into the cannula 70. The suture 20 may then be tied to the tissue to close a tear in the tissue with a pre-tied sliding knot, as shown in FIGS. 20-26. FIGS. 20-25 illustrate tying the knot before the knot is inserted a patient.

Figure 29:
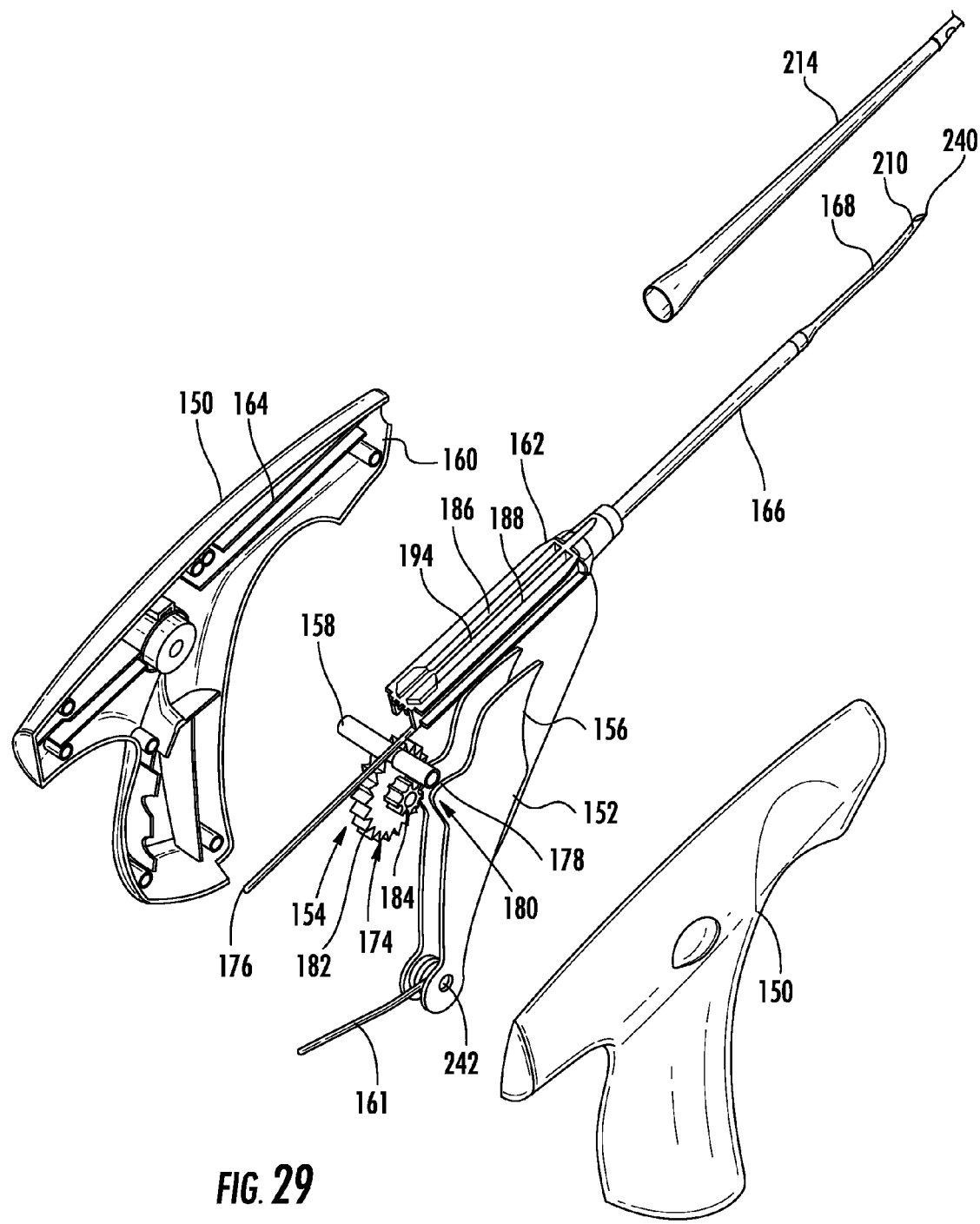
FIG. 29 is an exploded perspective view of another embodiment of the suture drive system.
Figure 30:
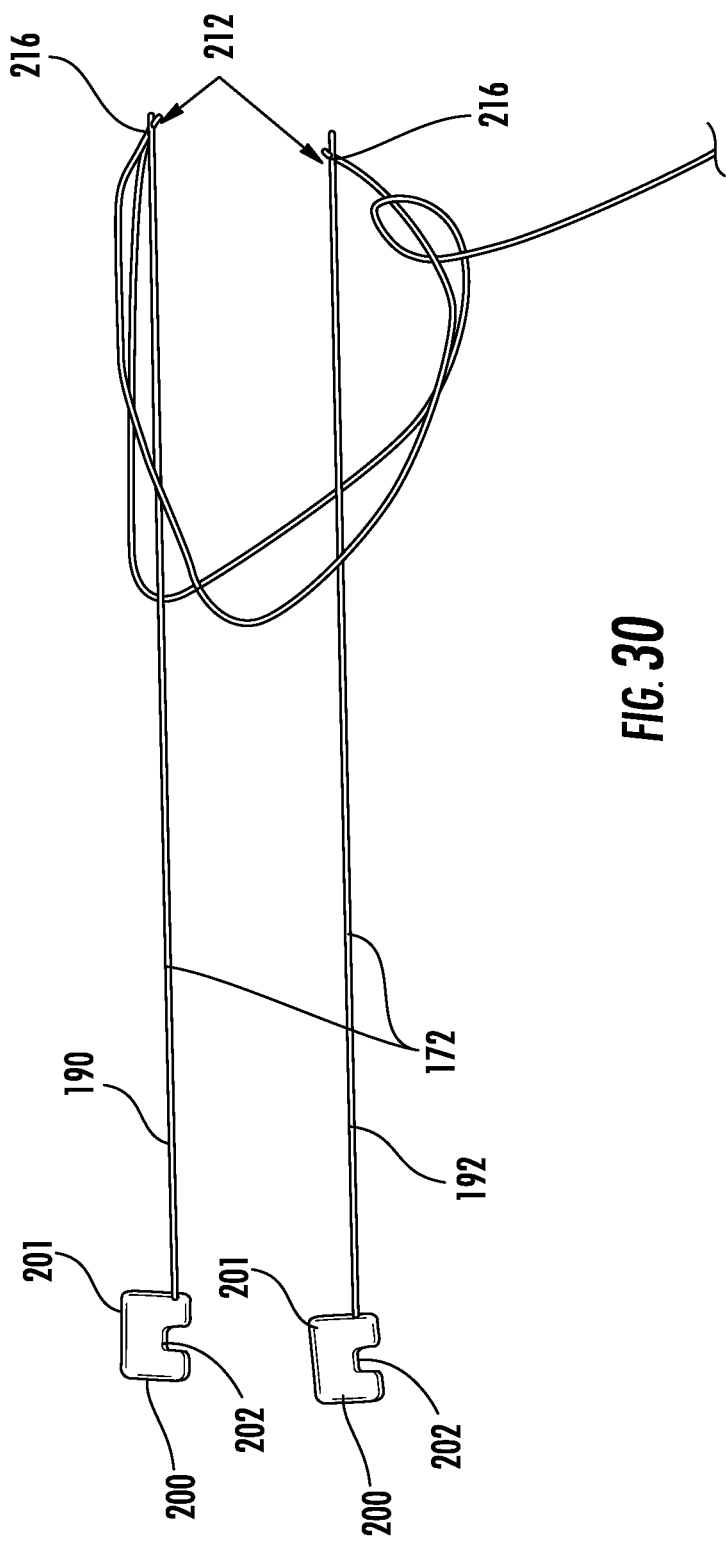
FIG. 30 is a side view of two push rods having anchors attached to distal ends of the rods and push rod guides attached to proximal ends of the push rods, wherein the push rods are configured to be usable within the system shown in FIG. 29.
Figure 31:
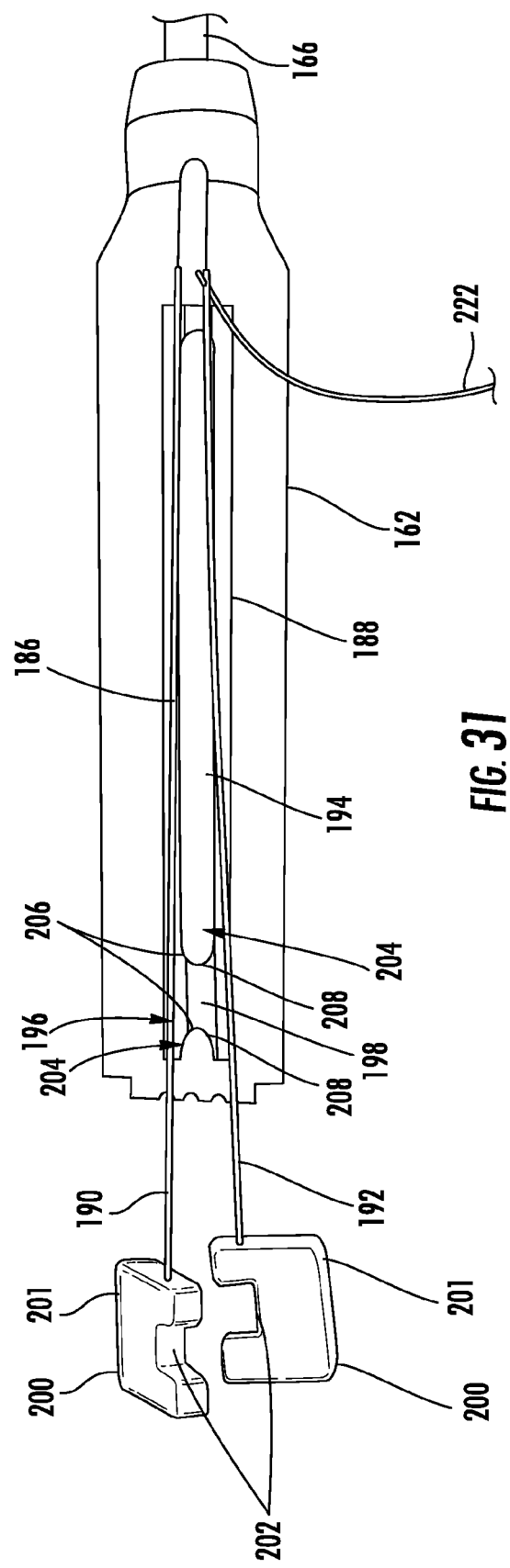
FIG. 31 is a perspective bottom view of two push rods of the system shown in FIG. 29 being inserted into a push rod guide support housing.
Figure 35:
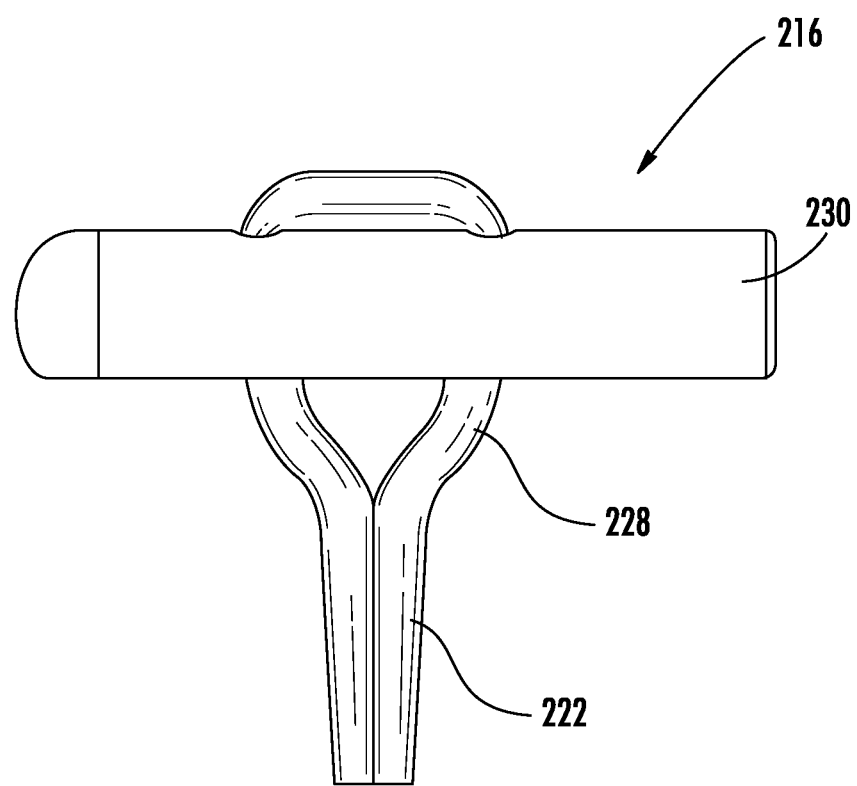
FIG. 35 is a side view of the anchor of FIG. 33 with a suture attached thereto.
Figure 36:
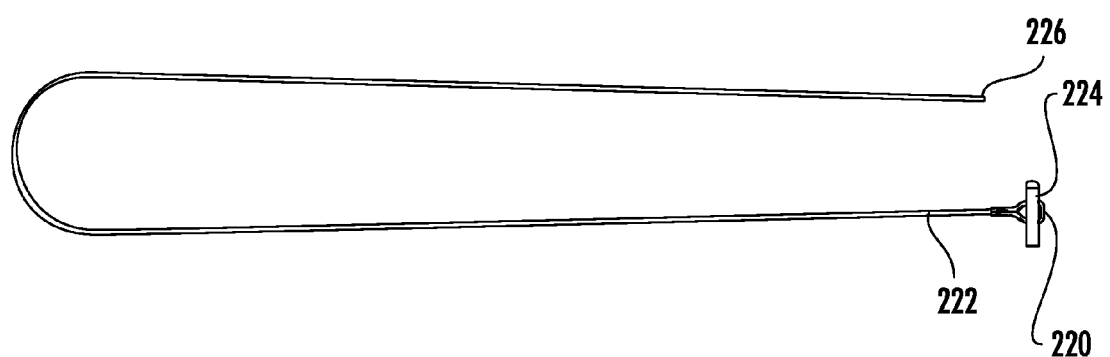
FIG. 36 is a side view of the anchor of FIG. 35 with a suture extending therefrom.
Figure 41:
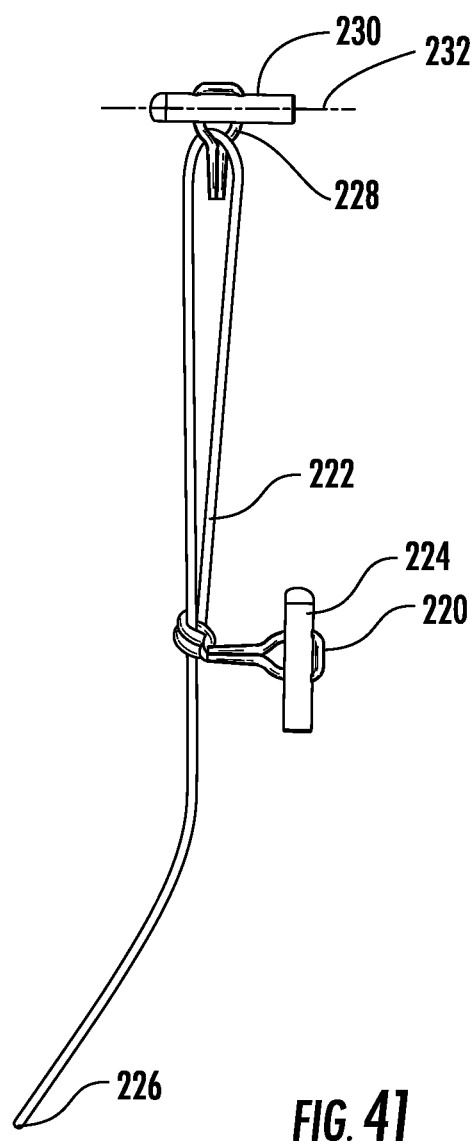

In another embodiment, as shown in FIGS. 29-47, the suture drive system 10 may be formed from a drive body 150 supporting a drive actuator 152 and drive mechanism 154 configured to be used to implement the outside-in technique. The suture drive system 10 may be shown assembled in FIG. 42 and exploded in FIG. 29. As shown in FIG. 29, the drive mechanism 154 may be formed from one or more gears 174 in communication with a first linear gear 176 forming a rack and pinion drive mechanism. In particular, the drive actuator 152 may include a second linear gear 178 configured to engage the gear 174, which is in turn configured to engage the first linear gear 176. The first linear gear 176 may be positionable via a push rod selector 158 to advance a push rod 172 within a cannula 166. The push rod selector 158 may have at least a portion extending outside of the drive body 150. The second linear gear 178 may be positioned on a proximal end 180 of the drive actuator 152 in close proximity to the drive mechanism 154. The first linear gear 176 may include teeth in contact with teeth extending from the bottom of the gear 174, and the second linear gear 178 may include teeth in contact with teeth extending from the top of the gear 174.

In another embodiment, the gear 174 may be formed from a first gear 182 in contact with the first linear gear 176 and a second gear 184 in contact with the second linear gear 178.

The first gear 182 may be rigidly coupled to the second gear 184, and the first gear 182 may be larger than the second gear 184. As such, a mechanical advantage can be created such that they first linear gear 176 may travel further than the linear travel of the second linear gear 178. In one embodiment, a trigger 154 coupled to the drive actuator 152 may be advanced one unit of measurement, while the cannula 166 to which the drive mechanism 152 is attached is advanced linearly more than one unit due to the mechanical advantage created by the size difference between the first and second gears 182, 184. The system may include one or more triggers 156 configured to actuate the drive actuator 152. The trigger 156 may be biased away from the drive body 150 via a spring 161, such as, but not limited to, a torsion spring.

As shown in FIGS. 29, 31, 43-47, the suture drive system 10 may also include one or more push rod guide support housings 162 positioned within a push rod guide support housing receiving chamber 164 in the drive body 150. The push rod guide support housing 162 may include first and second linear push rod guide receiving channels 186, 188 extending longitudinally therein and housing first and second linear push rods 190, 192. An alignment rib 194 may separate the first and second linear push rod guide receiving channels 186, 188. A proximal end 196 of the alignment rib 194 may include a push rod engaging slot 198 which may be configured to receive a push rod driver 244 extending from the first linear gear 176 that is configured to engage a push rod guide 200 residing within at least one of the first and second linear push rod guide receiving channels 186,188. The push rod driver 244 may be a protrusion having any appropriate shape and configuration. The push rod selector 158 may include one or more arms 246 for keeping the push rod driver in the first and second linear push rod receiving channels 186, 188.

In at least one embodiment, each of the first and second linear push rod receiving channels 186, 188 may include a push rod guide 200 coupled to a push rod 172. The push rod guide 200 may include a collar 201 positioned on an upper surface of the push rod guide 200 that rides on top of the push rod guide support housing 162 which prevents rotation of the push rod guide 200. The collar 201 may have a larger cross-sectional area than remaining portions of the push rod guide 200 to limit movement. In addition, movement of the push rod guide 200 is limited to being axially in a direction parallel to the push rod 172 positioned within the cannula 166.

Each push rod guide 200 may include a first linear gear receiving slot 202 extending into the bottom of the push rod guide 200. The first linear gear receiving slot 202 may be configured such that when the push rod guide 200 is positioned in the one of the first and second linear push rod guide receiving channels 186, 188, the first linear gear receiving slot 202 may be positioned adjacent to the push rod engaging slot 198 positioned in the alignment rib 194. The side walls 204 of the push rod engaging slot 198 may include first and second angled deflector surfaces 206, 208 that are joined at a point in the middle of the alignment rib 194. The point at the intersection of each of the first and second angled deflector surfaces 206, 208 is directed towards the other pointed side wall 204. In such a position, the push rod engaging slot 198 enables a push rod selector 158 to move the first linear gear 176 from the first linear push rod guide receiving channel 186 to the second linear push rod guide receiving channel 188, or vice versa, when the push rod selector 158 may be partially misaligned with the push rod engaging slot 198.

As shown in FIGS. 29 and 32, the suture drive system 10 may include one or more cannula support chambers 160 in the drive body 150. The suture drive system 10 may also include one or more cannulas 166 having an inner channel 168 configured to receive one or more push rods 172. The inner channel 168 of the cannula 166 may be configured to receive at least a portion of two push rods 172 simultaneously within at least a portion of the at least one cannula 166 and having a distal window 210 through which distal ends 212 of the push rods 172 extend. The cannula 166 may be straight or have another appropriate configuration. In at least one embodiment, the cannula 166 may include a distal tip curved about 15 degrees and about 30 degrees.

As shown in FIGS. 30 and 33-41, the suture drive system 10 may include two push rods 172 and may include an anchor 216 releasably affixed to a distal end 212 of each of the push rods 172. The anchors 216 may be elongated, tubular members and may be formed from PEEK or other appropriate material. A first end 220 of a suture 222 may be secured to a first anchor 224, and a second end 226 of the suture 222 extends through a loop 228 attached to a second anchor 230. The first end 220 of the suture 222, after extending through the loop 228 in the second anchor 230, may form a slip knot. The first end 220 of the suture 222, after extending through the loop 228 in the second anchor 230, may form a figure eight knot. The second anchor 230 may be an elongated member, and the loop 228 may pierce the second anchor 230 twice through an outer surface and generally orthogonal to a longitudinal axis 232 of the elongated member forming the second anchor 230. As shown in FIGS. 33 and 34, the anchors 216 may have a flat surface 234 through which two orifices 236, 238 protrude. The flat surface 234 provides space for the loop 228 and suture 222 to fit within the cannula 166 with the push rod 172. The suture 222 extends through the cannula 166 and partially resides in the drive body 150.

Figure 42:
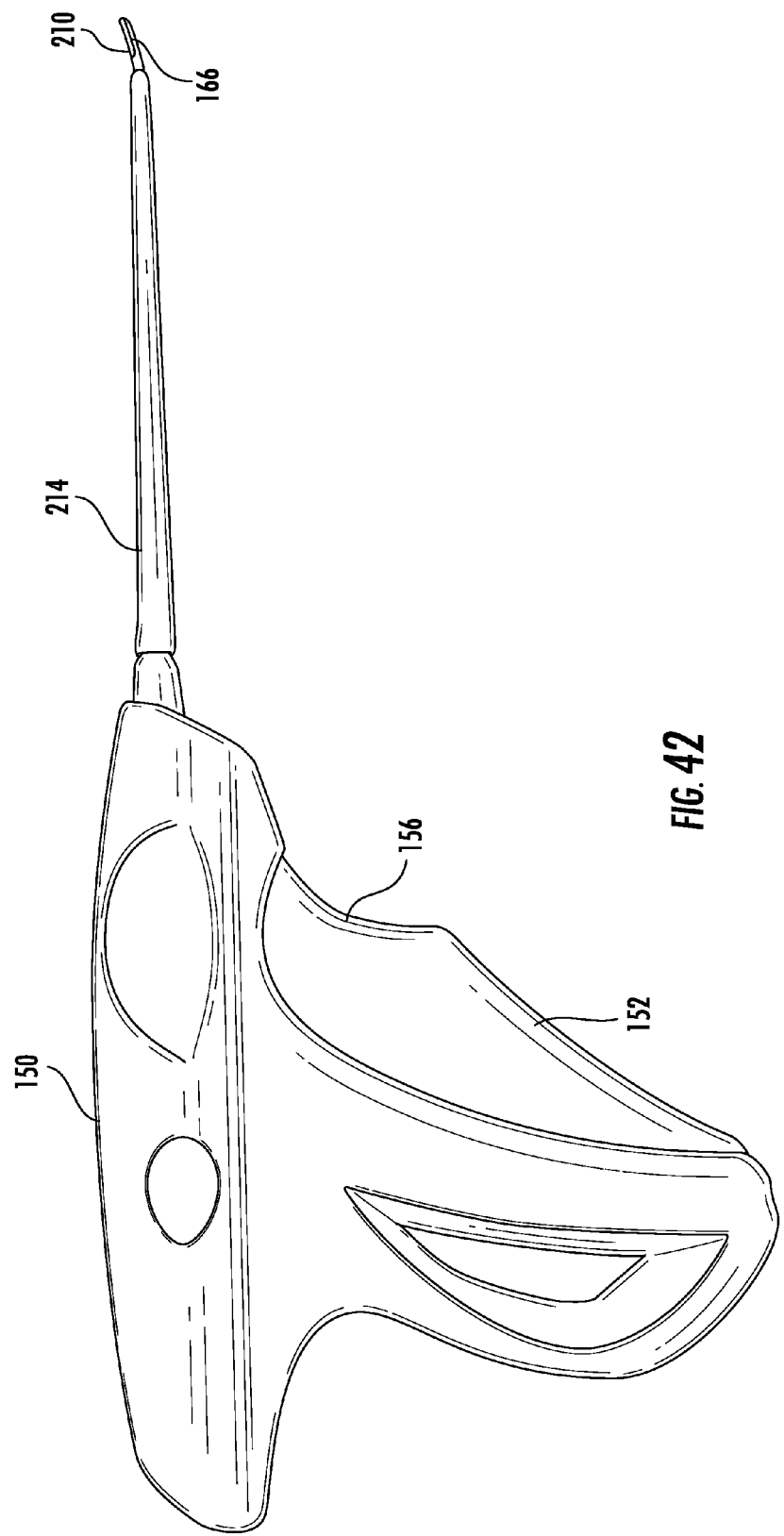
FIG. 42 is a side view of the suture drive system shown in FIGS. 29-41.
Figure 43:
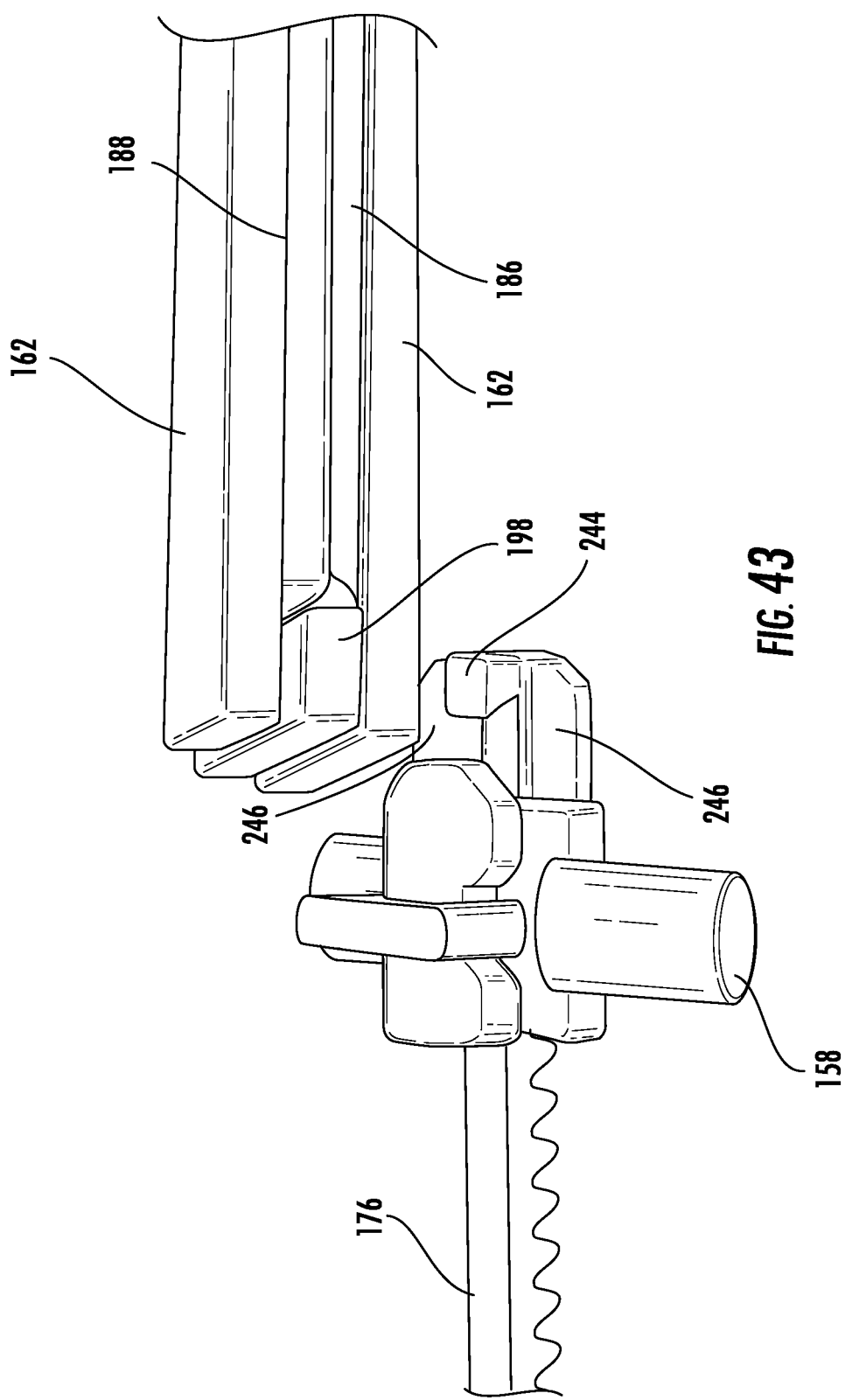
FIG. 43 is a partial perspective view of the first linear gear attached to the push rod selector and partially removed from being engagement with a push rod guide in the push rod guide support housing.
Figure 44:
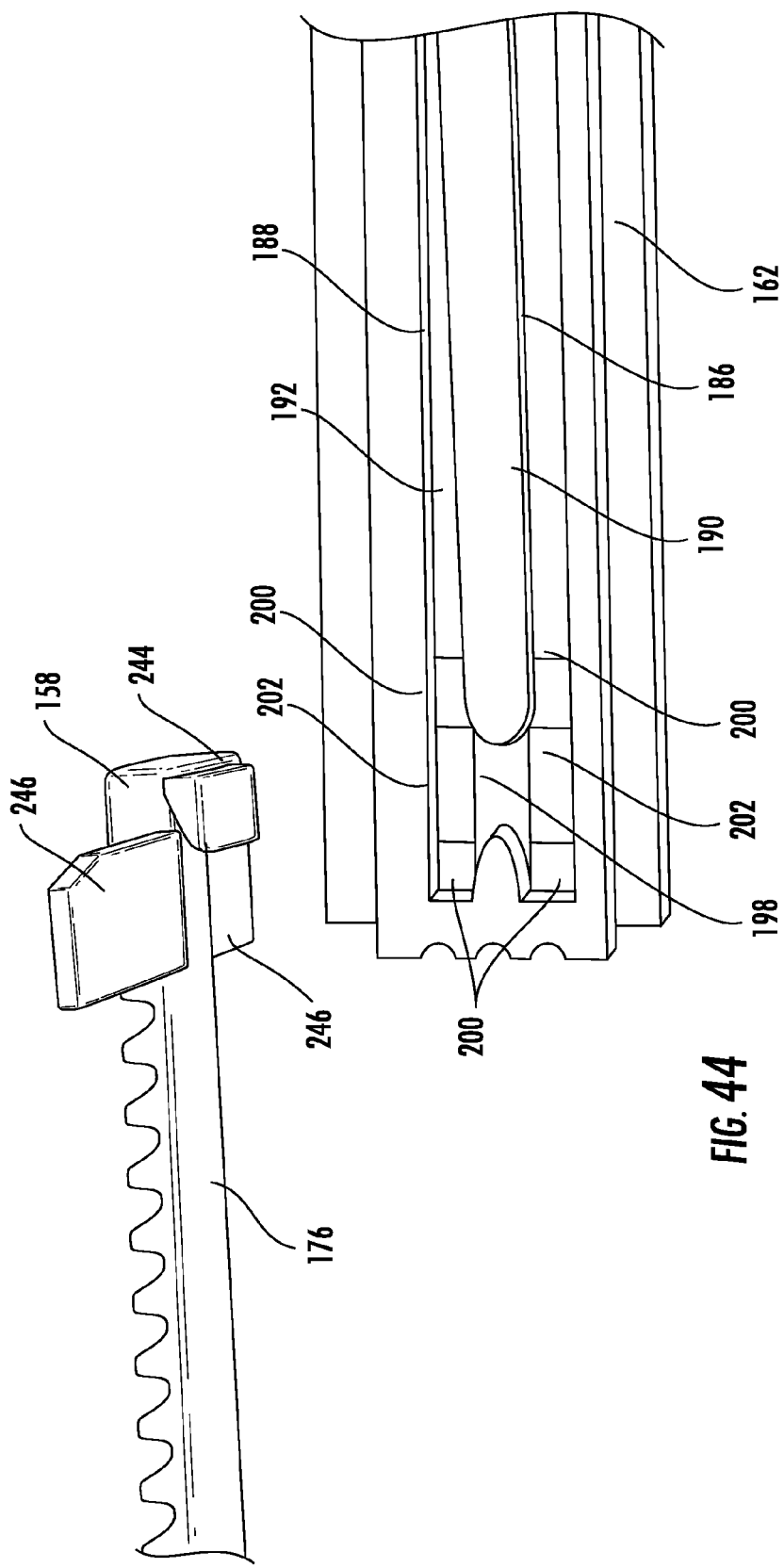
FIG. 44 is another partial perspective view of the first linear gear attached to the push rod selector and partially removed from being engagement with a push rod guide in the push rod guide support housing.
Figure 45:
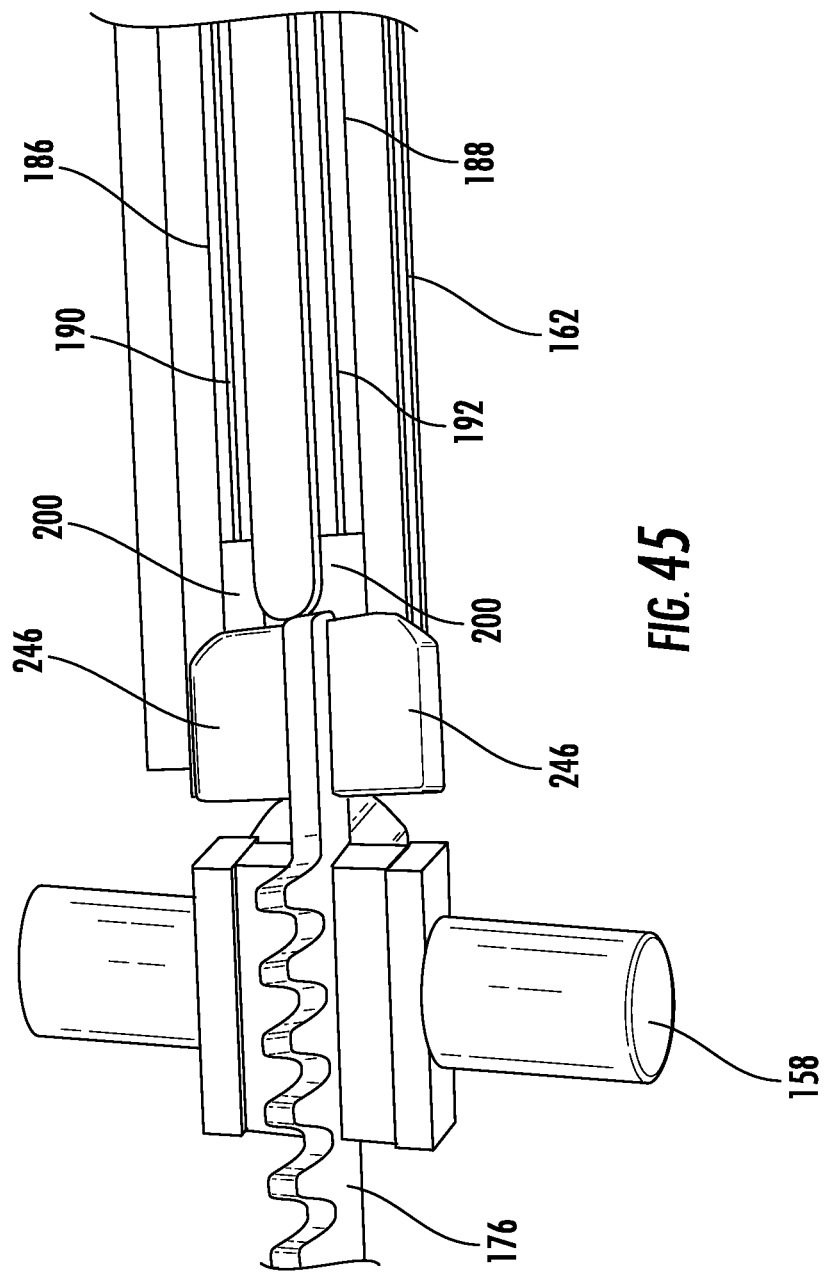
FIG. 45 a partial perspective view of the first linear gear attached to the push rod selector and engaged with a push rod guide in the push rod guide support housing.

The suture drive system 10 may also include a depth stop 214, as shown in FIGS. 29 and 42, formed from a tubular body sized to fit over the cannula 166. The depth stop 214 may be configured such that the length of the depth stop 214 may be adjustable. In at least one embodiment of the system 10 shown in FIGS. 29-36, the drive body 150, the drive actuator 152, driver mechanism 154, cannula 166 and other components may be disposable, and as such may be formed from materials, such as, but not limited to, plastic.

During use, the suture drive system 10 may be used to install a suture system into tissue, which may or may not be within a patient. Before installation of a suture 222, shown in FIGS. 29-36, into the tissue, a user, such as a medical doctor, may insert a distal tip 240 of the cannula 166 into incisions made in a patient until the tip 240 contacts the tissue in which the suture 222 is desired to be inserted. The outside-in suture method is employed using the system 10 shown in FIGS. 29-41. As such, the cannula 166 may be inserted through the tissue before the trigger 156 is squeezed. The drive actuator 152 may be activated by squeezing the trigger 156 towards the handle, as shown in FIG. 29. The actuator 152 may pivot about axis 242 of the drive actuator 152 thereby causing the trigger 156 to move the second linear gear 178 towards the second gear 184, which in turn causes the second gear 184 to rotate. The second gear 184 causes the first gear 182 to rotate, which in turn causes the first linear gear 176 to move in a direction opposite to the direction of movement of the second linear gear 178.

Figure 46:
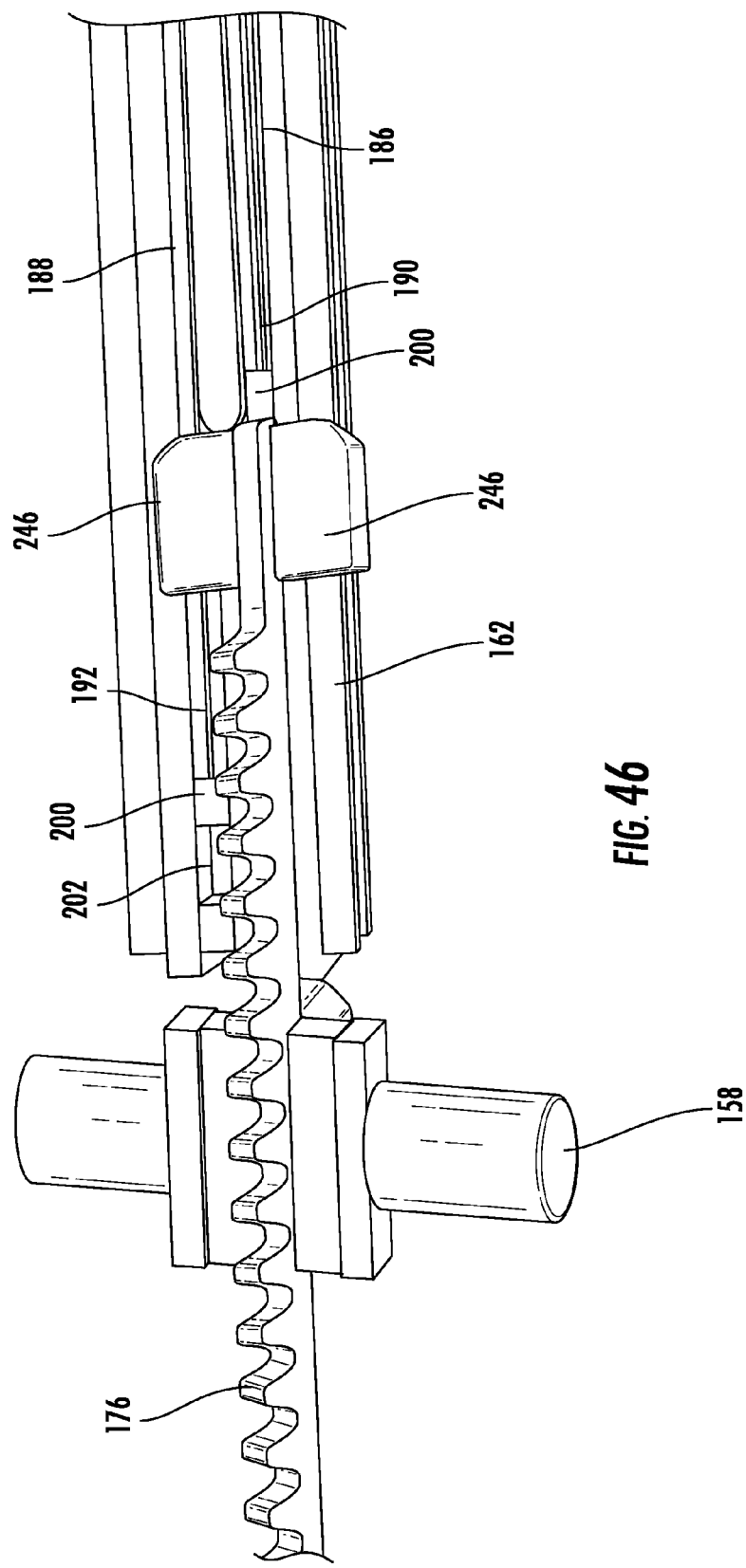
FIG. 46 is a partial perspective view of the first linear gear attached to the push rod selector and engaged with a push rod guide in the second linear push rod guide receiving channel in the push rod guide support housing.
Figure 47:
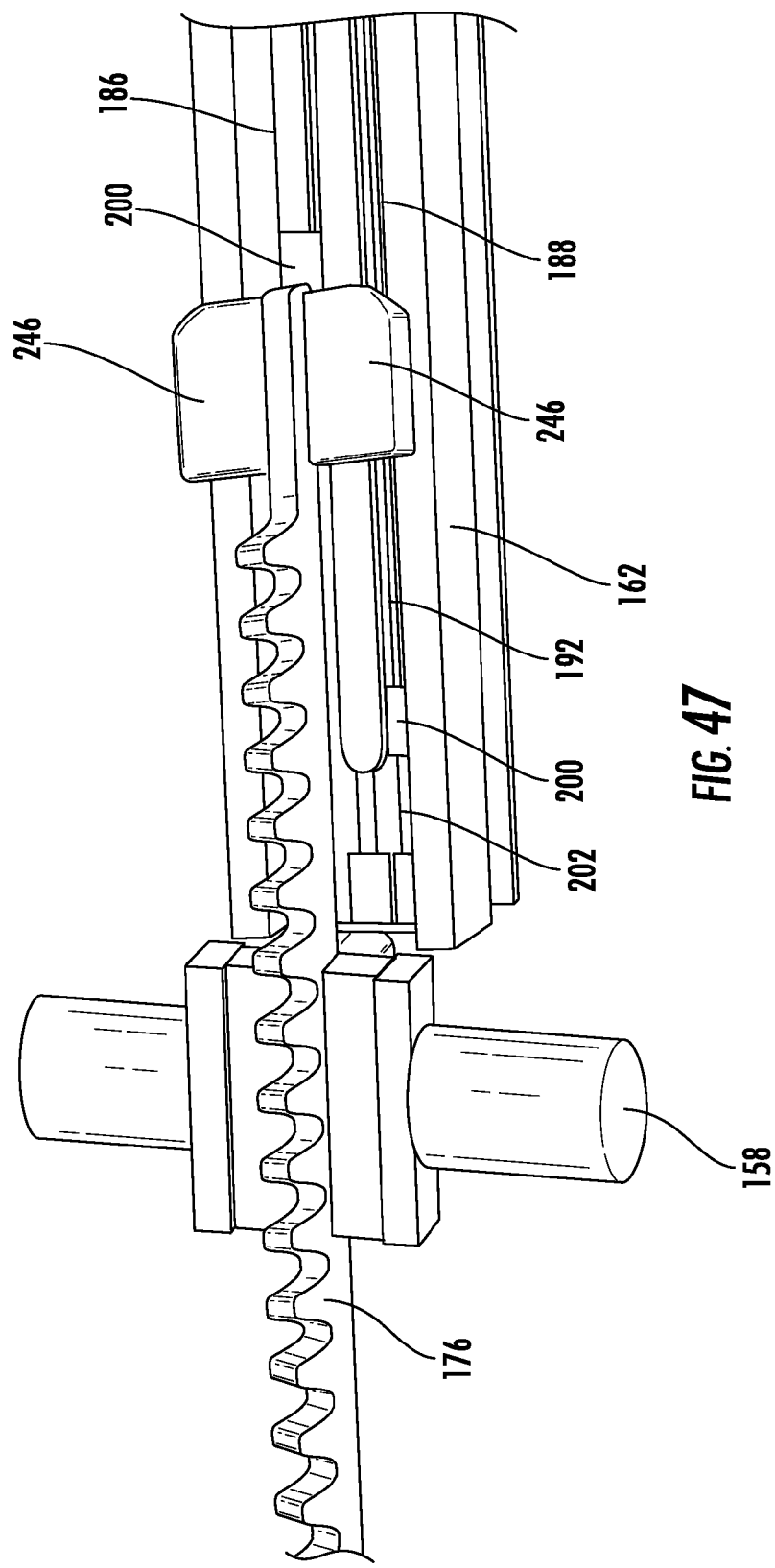
FIG. 47 is a partial perspective view of the first linear gear attached to the push rod selector and engaged with a push rod guide in the first linear push rod guide receiving channel in the push rod guide support housing.

The first linear gear 176 advances the push rod 172 in line with the push rod selector 158, as shown in FIG. 46. The push rod 200 in the first linear push rod receiving channel 186 pushes the first push rod 190 through the cannula 166 into the tissue. Once the trigger 156 has been fully depressed, the first anchor 224 is deployed in the tissue and the first push rod 190 is withdrawn into the cannula 166. The push rod selector 158 is then pushed toward the drive body 150, which causes the trigger 156 to be shifted from the first linear push rod guide receiving channel 186 to the first linear push rod guide receiving channel 188. The second anchor 230 may then be installed in the tissue in the same manner as described for the first anchor 224, as shown in FIG. 47, and the second push rod 192 may then be retracted into the cannula 166. The pre-tied sliding knot can be tensioned to secure the suture 20 to the tissue to close a tear in the tissue with a knot as shown in FIGS. 37-41.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A suture drive system, comprising:
    a drive body supporting a drive actuator and drive mechanism;
    at least one trigger configured to actuate the drive actuator;
    a push rod selector with at least a portion extending outside of the drive body;
    at least one cannula support chamber;
    a push rod guide support housing positioned within a push rod guide support housing receiving chamber in the drive body;
    at least one cannula having an inner channel configured to receive at least one drive shaft coupled to at least one push rod; and
    the push rod guide support housing includes first and second linear push rod guide receiving channels extending longitudinally therein and housing first and second linear push rods;
    wherein the drive mechanism is formed from at least one gear in communication with a first linear gear forming a rack and pinion drive mechanism, wherein the drive actuator includes a second linear gear configured to engage the at least one gear, wherein the first linear gear is positionable via the push rod selector to advance the at least one push rod within the cannula, and wherein the second linear gear is positioned on a proximal end of the drive actuator in close proximity to the drive mechanism;
    wherein the push rod guide support housing comprises first and second linear push rod guide receiving channels extending longitudinally therein and housing first and second linear push rods, further comprising an alignment rib separating the first and second linear push rod guide receiving channels, wherein a proximal end of the alignment rib includes a push rod engaging slot which is configured to receive a portion of the push rod selector configured for lateral movement through the push rod engaging slot; and
    wherein the first linear gear includes a push rod driver extending from the first linear gear, wherein the push rod driver contacts one of the first and second linear push rods.

2. The suture drive system of claim 1, wherein the inner channel of the at least one cannula is configured to receive at least a portion of two push rods simultaneously within at least a portion of the at least one cannula and having a distal window through which distal ends of the push rods extend.

3. The suture drive system of claim 1, further comprising at least one push rod guide coupled to at least one of the first and second linear push rods, and wherein the push rod driver extending from the first linear gear is configured to reside within a first linear gear receiving slot in the at least one push rod guide.

4. The suture drive system of claim 3, wherein the at least one push rod guide further comprises at least one collar configured to prevent rotation of the at least one push rod guide within the first linear push rod guide receiving channel in the push rod guide support housing.

5. A suture drive system, comprising:
    a drive body supporting a drive actuator and drive mechanism;
    at least one trigger configured to actuate the drive actuator;
    a push rod selector with at least a portion extending outside of the drive body;
    at least one cannula support chamber;
    a push rod guide support housing positioned within a push rod guide support housing receiving chamber in the drive body;
    at least one cannula having an inner channel configured to receive at least one drive shaft coupled to at least one push rod; and the push rod guide support housing includes first and second linear push rod guide receiving channels extending longitudinally therein and housing first and second linear push rods;
    wherein the drive mechanism is formed from at least one gear in communication with a first linear gear forming a rack and pinion drive mechanism, wherein the drive actuator includes a second linear gear configured to engage the at least one gear, wherein the first linear gear is positionable via the push rod selector to advance the at least one push rod within the cannula, and wherein the second linear gear is positioned on a proximal end of the drive actuator in close proximity to the drive mechanism;
    an anchor releasably affixed to a distal end of each of the push rods, wherein a first end of a suture is secured to a first anchor affixed to the first push rod, and a second end of the suture extends through a loop attached to a second anchor affixed to the second pushrod, and wherein the second anchor is an elongated member, and the loop pierces the second anchor twice through an outer surface and generally orthogonal to a longitudinal axis of the elongated member; and
    wherein the push rod guide support housing comprises first and second linear push rod guide receiving channels extending longitudinally therein and housing first and second linear push rods, further comprising an alignment rib separating the first and second linear push rod guide receiving channels and wherein a proximal end of the alignment rib includes a push rod engaging slot which is configured to receive a portion of the push rod selector configured for lateral movement through the push rod engaging slot and is configured to engage a push rod guide residing within one of the first and second linear push rod guide receiving channels.

6. The suture drive system of claim 5, wherein the inner channel of the at least one cannula is configured to receive at least a portion of two push rods simultaneously within at least a portion of the at least one cannula and having a distal window through which distal ends of the push rods extend.

7. The suture drive system of claim 5, further comprising at least one push rod guide coupled to at least one of the first and second linear push rods, and wherein the push rod driver extending from the first linear gear is configured to reside within a first linear gear receiving slot in the at least one push rod guide.

8. The suture drive system of claim 7, wherein the at least one push rod guide further comprises at least one collar configured to prevent rotation of the at least one push rod guide within the first linear push rod guide receiving channel in the push rod guide support housing.

* * * * *